United States Patent
Stewart et al.

(10) Patent No.: US 6,762,334 B1
(45) Date of Patent: *Jul. 13, 2004

(54) ALKYLAROMATIC PROCESS WITH REMOVAL OF AROMATIC BYPRODUCTS USING EFFICIENT DISTILLATION

(75) Inventors: Douglas G. Stewart, Wheeling, IL (US); Dennis E. O'Brien, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/192,680

(22) Filed: Jul. 9, 2002

Related U.S. Application Data

(63) Continuation of application No. 09/793,260, filed on Feb. 26, 2001, now Pat. No. 6,417,420.

(51) Int. Cl.[7] .................... C07C 2/64; C07C 25/067; C07C 25/107; C07C 2/00
(52) U.S. Cl. .................. 585/323; 585/449; 585/450; 585/455; 585/446
(58) Field of Search .................. 585/323, 449, 585/450, 455, 446

(56) References Cited

U.S. PATENT DOCUMENTS

| | | | |
|---|---|---|---|
| 2,471,134 A | 5/1949 | Wright | 196/100 |
| 4,587,370 A | 5/1986 | DeGraff | 585/450 |
| 5,276,231 A | 1/1994 | Kocal et al. | 585/323 |
| 5,334,793 A | 8/1994 | Kocal | 585/323 |
| 6,069,285 A | 5/2000 | Fritsch et al. | 585/449 |
| 6,417,420 B1 * | 7/2002 | Stewart et al. | 585/323 |

OTHER PUBLICATIONS

Briones, V. et al. *Pinch Analysis Used in Retrofit Design of Distillation Units* Oil and Gas Journal, Jun. 21, 1999 pp. 41–46.
Schulz, R.C. et al. *LAB Production* $2^{nd}$ World Conference on Detergents Montreux, Switzerland Oct. 5–10, 1986.
Meyers, R.A. *Handbook of Petroleum Refining Processes* McGraw–Hill, New York, $2^{nd}$ Ed., 1997 Chapters 1.5 and 5.2.
Nelson, W.L. *Petroleum Refinery Engineering* McGraw–Hill, New York, $1^{st}$ Ed. $4^{th}$ Impression, 1936, p. 442, fig. 141.
Watkins, R.N. *Petroleum Refinery Distillation* Gulf Publishing Company, Book Div., Houston, TX, $2^{nd}$ Ed. May 1981, pp. 101–103 and 114–115.
Triantafyllou, C. et al. *The Design and Optimisation of Fully Thermally Coupled Distillation Columns* Trans IChemE, vol. 70, Part A, Mar. 1992, pp. 118–132.
Kaibel, G., *Distillation Columns with Vertical Partitions*, Chem. Eng. Technol. 10(1987) pp. 92–98.

* cited by examiner

*Primary Examiner*—Thuan D Dang
(74) *Attorney, Agent, or Firm*—John G. Tolomei; James C. Paschall; Michael A. Moore

(57) ABSTRACT

A process for the production of alkylaromatic hydrocarbons by alkylating aromatic hydrocarbons with olefinic hydrocarbons is disclosed. The olefinic hydrocarbons are produced by dehydrogenating paraffinic hydrocarbons. Aromatic byproducts formed in dehydrogenation are removed using an aromatic byproducts removal zone and either a dividing wall distillation column or thermally coupled distillation columns. The process significantly decreases the cost of utilities in producing alkylaromatics, such as precursors for detergent manufacture.

41 Claims, 3 Drawing Sheets

ALKYLAROMATIC PROCESS WITH REMOVAL OF AROMATIC BYPRODUCTS USING EFFICIENT DISTILLATION

CROSS-REFERENCE TO RELATED APPLICATION

This application is a continuation of U.S. application Ser. No. 09/793,260 filed Feb. 26, 2001, now U.S. Pat. No. 6,417,420 the entire contents of which are hereby incorporated by reference.

FIELD OF THE INVENTION

This invention is an improvement in a process for the production of alkylated aromatic compounds.

BACKGROUND OF THE INVENTION

Nearly forty years ago, it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured worldwide. LABS are manufactured from linear alkyl benzenes (LAB). The petrochemical industry produces LAB by dehydrogenating linear paraffins to linear olefins and then alkylating benzene with the linear olefins in the presence of HF or a solid alkylation catalyst. The linear paraffins are straight chain (unbranched) or normal paraffins. Normally, the linear paraffins are a mixture of linear paraffins having different carbon numbers. The linear paraffins have generally from about 6 to about 22, preferably from 10 to 15, and more preferably from 10 to 12 or from 11 to 13, carbon atoms per molecule.

LAB processes are described in the book edited by R. A. Meyers entitled "Handbook of Petroleum Refining Processes" (McGraw Hill, N.Y. 1986) and "Ullmann's Encyclopedia of Industrial Chemistry," Volumes A8 and A13, Fifth Edition (VCH, Weinheim, Germany). Flow schemes are illustrated in U.S. Pat. No. 3,484,498 issued to R. C. Berg, U.S. Pat. No. 3,494,971 issued to E. R. Fenske, U.S. Pat. No. 4,523,048 issued to Vora which teaches use of a selective diolefin hydrogenation zone, and U.S. Pat. No. 5,012,021 issued to B. Vora which teaches use of a selective monoolefin hydrogenation zone. Solid alkylation catalysts are illustrated in U.S. Pat. No. 3,201,487 issued to S. Kovach et al.; U.S. Pat. No. 4,358,628 issued to L. Slaugh; U.S. Pat. No. 4,489,213 issued to S. Kovach; and U.S. Pat. No. 4,673,679 issued to D. Farcasiu. Zeolitic solid alkylation catalysts are disclosed in U.S. Pat. Nos. 3,751,506; 4,387,259; and 4,409,412.

It is well known that aromatic byproducts are formed during the catalytic dehydrogenation of paraffins. For instance, the article starting at page 86 of the Jan. 26, 1970 issue of "Chemical Engineering" states that the product of the dehydrogenation of linear paraffins includes aromatic compounds. The nature of the particular aromatic byproducts that are formed in dehydrogenation is not essential to this invention. Without limiting this invention in any way, these aromatic byproducts are believed to include, for example, alkylated benzenes, dialkylated benzenes, naphthalenes, other polynuclear aromatics, diphenyl compounds, alkylated polynuclear hydrocarbons in the $C_{10}$–$C_{15}$ range, indanes, and tetralins, that is, they are aromatics of the same carbon number as the paraffin being dehydrogenated and may be viewed as aromatized normal paraffins. Some aromatic byproducts may be more detrimental than others in deactivating solid alkylation catalysts. It is believed that aromatic byproducts with few or small alkyl groups are more detrimental to solid alkylation catalysts than aromatic byproducts with multiple or long alkyl groups. It is also believed that aromatic byproducts having multiple aromatic rings are more detrimental to solid alkylation catalysts than aromatic byproducts having single aromatic rings. The particular side reactions that lead to the formation of the aromatic byproducts are also not essential to this invention. Again, without limiting this invention in any way, an illustration of some of the parallel thermal cracking reactions that can lead to the formation of aromatic byproducts is found in the diagram at the top of page 4–37 of the book mentioned above entitled "Handbook of Petroleum Refining Processes". Typically, from about 0.2 to about 0.7 weight percent, and generally to the extent of no more than 1 weight percent, of the feed paraffinic compounds to a dehydrogenation zone form aromatic byproducts. Although some commercially available dehydrogenation catalysts are more selective than others at minimizing the formation of aromatic byproducts, it is believed that these byproducts are formed at least to a small extent at suitable dehydrogenation conditions in the presence of most if not all commercially available dehydrogenation catalysts. Since it is an economic advantage to operate the dehydrogenation zone at conditions that produce a high conversion of the feed paraffinic compounds and a high yield of the desired olefins, these aromatic byproducts are produced at least to a small extent in most if not all commercial dehydrogenation zones. But, since these aromatic byproducts have the same number of carbon atoms as both the unconverted feed paraffins and the product olefins, they have boiling points close to that of these paraffins and olefins. Thus, using conventional distillation, the aromatic byproducts are difficult to separate from a mixture such as the dehydrogenation effluent, which also contains these paraffins and olefins.

The aromatic byproducts from the dehydrogenation section enter the alkylation section. In the selective alkylation zone containing a solid alkylation catalyst, several possibilities can then occur. First, some of the aromatic byproducts deposit on the surface of the catalyst and as mentioned above deactivate the catalyst. Second, as mentioned above some of the aromatic byproducts are alkylated by monoolefins to form heavy alkylate. Each mole of heavy alkylate formed by this route represents the loss of two moles of feed paraffinic compound toward the production of a less-valuable product and reduces both dehydrogenation selectivity and alkylation selectivity. Third, some of the aromatic byproducts pass through the selective alkylation zone unreacted, are recovered with the overhead liquid stream of the paraffin column which is recycled to the dehydrogenation zone, and ultimately accumulate to unacceptable concentrations. In the prior art processes employing a solid alkylation catalyst, the concentration of aromatic byproducts in the stripping effluent stream can typically accumulate to 4–10 weight percent, which leads to rapid deactivation of solid alkylation catalyst. Where the alkylation catalyst is HF in the prior art processes, the concentration of aromatic byproducts in the stripping effluent stream can typically accumulate to 3–6 weight percent.

Processes for removing the aromatic byproducts that are formed during the catalytic dehydrogenation of paraffins are also known. Suitable aromatics removal zones may be selected from any processing methods that exhibit the primary requirement of selectivity for the aromatic byproducts.

Suitable aromatics removal zones include, for example, sorptive separation zones and liquid-liquid extraction zones. See U.S. Pat. No. 5,276,231 and U.S. Pat. No. 5,334,793, the contents of each are incorporated herein by reference. Where the aromatics removal zone is a sorptive separation zone, a fixed bed or a moving bed sorbent system may be used, but the fixed bed system is more common. The sorbent usually comprises a particulate material. In a fixed bed system, the sorbent is typically installed in one or more vessels in a parallel flow arrangement, so that when the sorbent bed in one vessel is spent by the accumulation of the aromatic byproducts thereon, the spent vessel is bypassed while continuing uninterrupted operation through another vessel. A purge stream comprising a purge component, such as $C_5$ or $C_6$ paraffin (e.g., normal pentane), is passed through the spent sorbent bed in the bypassed vessel in order to purge or displace unsorbed components of the stream containing the aromatic byproducts from the void volume between particles of sorbent. After purging, a regenerant or desorbent stream comprising a desorbent component such as $C_6$ or $C_7$ aromatic (e.g., benzene), is passed through the sorbent bed in the bypassed vessel in order to desorb aromatic byproducts from the sorbent. Following regeneration, the sorbent bed in the bypassed vessel is again available for use in sorbing aromatic byproducts.

Thus, a sorptive separation zone for removing the aromatic byproducts typically produces three effluents, which approximately correspond to each of the three steps in the cycle of sorption, purge, and desorption. The composition of each of the three effluents changes during the course of each step. The first effluent, the sorption effluent, contains unsorbed components (i.e., paraffins and olefins) of the stream from which the aromatic byproducts are removed, and also typically contains the desorbent component. With its decreased amount of aromatic byproducts relative to the stream that is passed to the sorptive separation zone, this effluent is used further along in the process to produce alkylaromatics. For example, if the stream that passes to the sorptive separation zone is the dehydrogenation zone effluent, the sorption effluent contains monoolefins and paraffins and thus passes directly to the alkylation zone.

The second effluent, the purging effluent, contains the purge component, unsorbed components of the stream from which the aromatic byproducts were sorbed, and often the desorbent component. The third effluent is the desorption effluent, which contains the desorbent component, the aromatic byproducts, and the purge component. In the typical prior art process, the purging and desorption effluents are separated in two distillation columns. The desorption effluent passes to one column, which produces an overhead stream containing the desorbent and purge components and a bottom stream containing the aromatic byproducts which is rejected from the process. The overhead stream of the first column and the purging effluent pass to a second column, which separates the entering hydrocarbons into an overhead stream containing the purge component and a bottom stream containing the desorbent component and unsorbed components of the stream from which the aromatic byproducts are removed. The overhead stream of the second column is used as the purge stream. The bottom stream of the second column is used in the process to produce alkylaromatics. In the example described above where the stream that passes to the sorptive separation zone is the dehydrogenation zone effluent, the bottom stream of the second column contains benzene, monoolefins, and paraffins and flows directly to the alkylation zone.

This two-column process for separating the purge and desorption effluents wastes energy. Energy is consumed to reboil the desorbent component (e.g., benzene) in the first column, to reboil the purge component (e.g., n-pentane) in the second column, and to heat the desorbent component in the second column. This process also has a high capital cost because two columns are needed. Thus, a process is sought in which the streams containing the aromatic byproducts, purge component, and desorbent component are produced in a more efficient manner that uses fewer utilities than the prior art two-column process.

Over fifty years ago, Wright proposed replacing two distillation columns with a single distillation column having a vertical partition (dividing wall column) within the column that would effect the separation of the column feed into three constituent fractions. It was recognized then that a dividing wall column could minimize the size or cost of the equipment needed to produce overhead, bottoms, and sidedraw products. See U.S. Pat. No. 2,471,134 (Wright). Wright described using the dividing wall column to separate a mixture of methane, ethane, propane, butanes, and a small amount of $C_5$ and heavier hydrocarbons.

Since then, researchers have studied the dividing wall column and have proposed using dividing wall columns for separating other mixtures, including xylenes (*Int. Chem. Engg.*, Vol. 5, No. 3, July 1965, 555–561); butanes and butenes (See e.g., *Trans IChemE*, Vol.70, Part A, March 1992, 118–132); methanol, isopropanol, and butanol (See e.g., *Trans IChemE*, Vol. 72, Part A, September 1994, 639–644); ethanol, propanol, and butanol (*Ind. Eng. Chem. Res.* 1995, 34, 2094–2103); air (See e.g., *Ind. Eng. Chem. Res.* 1996, 35, pages 1059–1071); natural gas liquids (*Chem. Engg.*, July 1997, 72–76); and benzene, toluene, and ortho-xylene (Paper No. 34 K, by M. Serra et al., prepared for presentation at the AIChE Meeting, Los Angeles, Calif., USA, November 1997). The Serra et al. paper also describes separating mixtures of butanes and pentane; pentanes, hexane, and heptane; and propane and butanes.

Despite the advantages of the dividing wall column and despite much research and study, the processing industry has long felt reluctant to use dividing wall columns in commercial processes. This widespread reluctance has been attributed to various concerns, including control problems, operational problems, complexity, simulation difficulties, and lack of design experience. See, for example, the articles by C. Triantafyllou and R. Smith in *Trans IChemE*, Vol. 70, Part A, March 1992, 118–132; F. Lestak and C. Collins in *Chem. Engg.*, July 1997, 72–76; and G. Duennebier and C. Pantelides in *Ind. Eng. Chem. Res.* 1999, 38, 162–176. The article by Lestak and Collins sets forth some general guidelines and considerations when substituting a dividing wall column for conventional columns. Nevertheless, the literature documents relatively few practical uses of dividing wall columns in commercial plants. See the article by H. Rudd in The Chemical Engineer, Distillation Supplement, Aug. 27, 1992, s14–s15 and the article in European Chemical News, Oct. 2–8, 1995, 26.

Prior art alkylaromatic processes, in particular, do not use dividing wall distillation columns. Nor do they use fully or non-fully thermally coupled distillation columns, which, as explained in the above-mentioned article by C. Triantafyllou and R. Smith, are thermodynamically equivalent to dividing wall columns when there is no heat transfer across the dividing wall. In particular, a dividing wall distillation column has not been used for separating the effluent streams from a sorptive separation step in an alkylaromatic process. This is not only for the reasons given above but also for three additional reasons. First, the focus of prior research studies has been on separating relatively unchanging mixtures of only a few (e.g., 3 to 5) components, whereas the purging effluent contains dozens of compounds and its composition changes gradually yet significantly from the start to the end of the purging step. In addition, the desorbent effluent likewise contains dozens of compounds, and its composition also changes to a significant extent over the course of the desorption step. Second, the research studies produce dividing wall distillation product streams in which co-boiling components are recovered in the same stream, whereas the separation of the purging and desorption effluents preferably produces the aromatic byproducts in one stream, so that they can be rejected from the process, and the monoolefins and paraffins in another stream for further use in the process. Third, achieving a commercially-useful long life of the solid alkylation catalysts used for the production of LAB requires that the composition of the stream containing the desorbent component be controlled relatively tightly, since the presence of aromatic byproducts in this stream tends to rapidly deactivate solid alkylation catalysts. Thus, alkylaromatic processes are characterized by changing compositions of the purging and desorbent effluents, unique requirements for the separation of co-boiling compounds, and a relatively tight specification on the aromatic byproducts in the stream containing the desorbent compounds. This combination compounds the problems, difficulties, and complexity of using a dividing wall distillation column or two thermally coupled distillation columns.

SUMMARY OF THE INVENTION

This invention is a process for the production of alkylaromatic hydrocarbons by alkylating feed aromatic hydrocarbons with olefinic hydrocarbons, where both olefinic hydrocarbons and aromatic byproducts are produced by dehydrogenating paraffinic hydrocarbons, and where the aromatic byproducts are removed using a aromatic byproducts removal zone and either a dividing wall distillation column or two thermally coupled distillation columns, where the two thermally coupled distillation columns are a prefractionator and a main column. It has now been recognized that use of two thermally coupled distillation columns or of a dividing wall distillation column rejects the aromatic byproducts in a manner that consumes less energy than the prior art process and yet is stable and controllable for commercial alkylaromatic production, despite the changing compositions of the effluents produced by the aromatic byproducts removal zone, unique requirements for the separation of the aromatic byproducts and the paraffinic hydrocarbons, and a relatively tight specification on the aromatic byproducts in the stream containing the desorbent compounds. As between a single dividing wall distillation column on the one hand and two fully thermally coupled distillation columns on the other hand, the former is preferred when the cost of a single distillation vessel represents a significant savings over that of two distillation vessels.

Accordingly, in a broad embodiment, this invention is a process for producing a product aromatic compound. A feed stream comprising a $C_6-C_{22}$ paraffin is dehydrogenated in a dehydrogenation zone. A dehydrogenated product stream comprising a monoolefin and aromatic byproducts is recovered from the dehydrogenation zone. At least a portion of the aromatics byproducts are selectively removed from the dehydrogenated product stream by at least intermittently passing at least a portion of the dehydrogenated product stream to an on-stream aromatic byproducts removal zone. The on-stream aromatic byproducts removal zone contains sorbent at conditions effective to selectively sorb the aromatic byproducts on the sorbent and to produce a sorption effluent stream comprising the monoolefin. At least a portion of the sorption effluent stream passes to a selective alkylation zone. In the selective alkylation zone, a feed aromatic compound is selectively alkylated by reacting the feed aromatic compound and the monoolefin to form a product aromatic compound. An alkylated product stream comprising the product aromatic compound is recovered from the selective alkylation zone. A purge stream comprising a purge component passes at least intermittently to an off-stream purge aromatic byproducts removal zone containing sorbent. The sorbent in the off-stream purge aromatic byproducts removal zone is contained in a sorbent bed having a void volume, and the void volume contains the $C_6-C_{22}$ paraffin or the monoolefin. The $C_6-C_{22}$ paraffin or the monoolefin is displaced from the void volume of the sorbent bed in the off-stream purge aromatic byproducts removal zone. A purging effluent stream comprising the $C_4-C_6$ paraffin and at least one of the $C_6-C_{22}$ paraffin and the monoolefin is produced. A desorbent stream comprising a desorption component passes at least intermittently to an off-stream desorption aromatic byproducts removal zone containing sorbent. The sorbent in the off-stream desorption aromatic byproducts removal zone contains sorbed aromatic byproducts. The aromatic byproducts are desorbed from the sorbent in the off-stream desorption aromatic byproducts removal zone, and a desorption effluent stream comprising the desorption component and the aromatic byproducts is produced. At least a portion of the desorption effluent stream passes at least intermittently to a first lateral section of an intermediate portion of a distillation column at distillation conditions. The first lateral section is separated from a second lateral section of the intermediate portion of the distillation column by a vertically oriented baffle extending upward from a lower portion of the distillation column to an upper portion of the distillation column. At least a portion of the purging effluent stream passes at least intermittently to the upper portion of the distillation column. The compounds entering the distillation column are separated to provide an overhead stream comprising the purge component, a sidedraw stream comprising the desorption component, and a bottom stream comprising the aromatic byproducts.

Other embodiments of the invention are set forth in the detailed description of the invention.

INFORMATION DISCLOSURE

Figure 1:
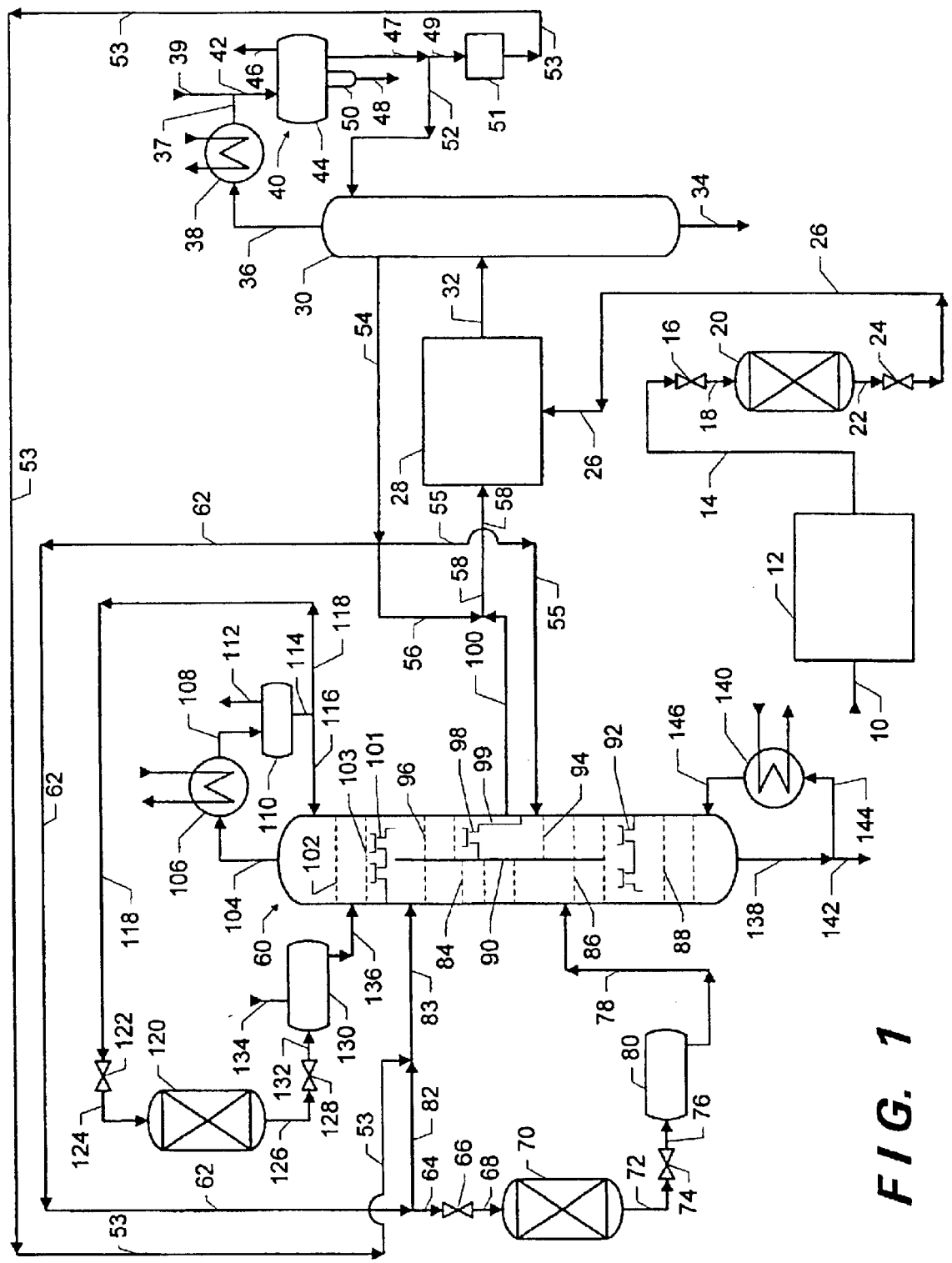
FIGS. 1–3 are process flow diagrams, each depicting an embodiment of the invention.

U.S. Pat. No. 2,471,134 (Wright) discloses a vertical fractionation column having a vertical partition that separates the feed inlet and a side stream outlet.

The article by C. Triantafyllou and R. Smith in Trans IChemE, Vol. 70, Part A, March 1992, starting at page 118 explains that a dividing wall distillation column is thermodynamically equivalent to a fully thermally coupled distillation column, provided that there is no heat transfer across the dividing wall.

The paper entitled *LAB Production*, by R. C. Schulz, P. R. Pujado, and B. V. Vora, presented at the $2^{nd}$ World Conference on Detergents, held at Montreux, Switzerland, during Oct. 5–10, 1986, describes an LAB process wherein feed treatment of the kerosene consists of prefractionation using a stripper and a rerun column followed by hydrotreating of the kerosene heartcut. The teachings of the Schulz et al. article are incorporated herein by reference. LAB processes are further described in the book edited by Robert A. Meyers entitled *Handbook of Petroleum Refining Processes*, (McGraw-Hill, New York, Second Edition, 1997) at Chapter 1.5, the teachings of which are incorporated herein by reference. Paraffin dehydrogenation processes are described in the Meyers book in Chapter 5.2, the teachings of which are incorporated herein by reference.

U.S. Pat. No. 4,587,370 (DeGraff) discloses a fractionation method that uses three fractionation columns employed in series for recovering product alkylaromatics produced by alkylation of feed aromatics. The overhead stream of the second column contains the product alkylaromatics and is employed as the heat source for the reboiler of the first column, which recycles feed aromatics to the alkylation reactor.

U.S. Pat. No. 5,276,231 (Kocal et al.) discloses a process for producing alkylated aromatic compounds by paraffin dehydrogenation and aromatic alkylation wherein aromatic byproducts formed in paraffin dehydrogenation are selectively removed using at least one aromatics removal zone.

U.S. Pat. No. 5,334,793 (Kocal) discloses a process for increasing catalyst life and improving product linearity in the alkylation of aromatics with linear olefins comprising decreasing the concentration in the alkylation feedstock of aromatic compounds formed in the dehydrogenation step.

U.S. Pat. No. 6,069,285 (Fritsch et al.) discloses an integrated alkylaromatic process using a solid alkylation catalyst and an aromatic rectifier that uses an aromatic byproducts removal zone.

The book entitled "Petroleum Refinery Engineering," written by W. L. Nelson, and published by McGraw-Hill Book Company, Inc., New York, First Edition, Fourth Impression, 1936, page 442, figure 141, shows a method of removing reflux heat using circulating reflux.

The book entitled, "Petroleum Refinery Distillation," written by R. N. Watkins, and published by Gulf Publishing Company, Book Division, Houston, Tex., Second Edition, May, 1981, pages 101–103 and 114–115, describes vacuum towers with pumpback and pumparound reflux heat removal.

The article written by Victor Briones, et al., which was published in Oil and Gas Journal, Jun. 21, 1999, beginning at page 41, describes using a pinch analysis method to design heat integration between atmospheric and vacuum units in a crude oil unit.

DETAILED DESCRIPTION

We shall first describe a typical process for the production of alkylated aromatic compounds without the removal of aromatic byproducts as currently and previously practiced along with some common variants of particular interest. We shall then describe how an aromatic byproducts removal zone may be incorporated into this typical process in order to properly set the stage upon which our invention is practiced and to emphasize that the success of our invention is not dependent upon the particular variant of the prior art used. We shall then describe the improvement which is our invention where it will become clear that its success is independent of the details of the prior art processes in which it is embedded.

The two feed compounds consumed in the subject process are a paraffinic and an aromatic compound. The paraffinic feed is preferably a straight chain (unbranched) or normal paraffin having from 6 to 22 carbon atoms per molecule. A better quality detergent precursor normally results from the use in the selective alkylation zone of an olefin having from about 10 to 15 carbon atoms per molecule. Therefore, a preferred paraffinic feed is a $C_{10}$ to $C_{15}$ paraffin or a $C_{10}$-plus linear paraffin. The paraffinic feed is normally a mixture of paraffins having different carbon numbers. A preferred method for the production of the paraffinic feed is the recovery of straight chain hydrocarbons from a hydrotreated kerosene boiling range petroleum fraction by extraction or by adsorptive separation. Suitable paraffinic feeds include $C_{10}$–$C_{22}$ linear paraffins, $C_{10}$–$C_{15}$ linear paraffins, and $C_{15}$–$C_{20}$ linear paraffins. In other applications of the subject process, the preferred paraffinic feed is a mixture of branched chain paraffinic compounds. These branched chain paraffinic feeds can be obtained by extraction, by adsorptive separation, or by suitable oligomerization and treatment processes. The aromatic feed which is alkylated in the subject process is preferably to benzene, but the aromatic feed may also be of a higher molecular weight, such as toluene, a xylene, ethylbenzene, phenol, naphthalene, etc.

For purposes of discussion, the typical process may be divided into a dehydrogenation section and an alkylation section. The dehydrogenation section will preferably be configured substantially in the following manner. A feed stream containing paraffins combines with recycled hydrogen and recycled unreacted paraffins from the alkylation section. This forms a reactant stream which is heated and passed through a bed of a suitable catalyst maintained at the proper dehydrogenation conditions of temperature, pressure, etc. The effluent of this catalyst bed or reactor effluent stream is usually cooled, partially condensed, and passed to a vapor-liquid or product separator. The condensed material, referred to herein as the dehydrogenated product stream, is passed to a stripping separation zone which usually includes a stripping column that removes all compounds which are more volatile than the lightest normal hydrocarbon which it is desired to charge to the alkylation section of the process. The stripping column produces a net bottoms stream referred to herein as the stripping effluent stream.

Dehydrogenation catalysts are well known in the prior art as exemplified by U.S. Pat. Nos. 3,274,287; 3,315,007; 3,315,008; 3,745,112; and 4,430,517. What is important is that catalysts for dehydrogenation are well known to those skilled in the dehydrogenation art and need not be described here in great detail. The nature of the dehydrogenation catalyst is not critical to the success of the subject invention and is largely a matter of choice to be made by the practitioner.

The stripping effluent stream is passed to an alkylation section which comprises a selective alkylation zone and a distillation or alkylate recovery zone. In the selective alkylation zone, linear olefins in the stripping effluent stream react with a feed stream containing an aromatic which is generally benzene to produce a selective alkylation zone effluent stream containing linear alkylbenzene. The selective alkylation zone can have a number of different configurations and reactor vessels depending on whether the catalyst is HF or a solid alkylation catalyst. Solid alkylation catalysts typically are characterized as having an acid function and are, therefore, better known as solid acid catalysts. Such solid acid catalysts include, but are not limited to, materials such as amorphous silica-alumina, crystalline aluminosilicate materials such as zeolites and molecular sieves, naturally occurring and man-made clays including pillared clays, sulfated oxides such as sulfonated zirconia, traditional Friedel-Crafts catalysts such as aluminum chloride and zinc chloride, and solid Lewis acids generally. Again, what is important is that processes and catalysts for alkylation are well known to those skilled in the alkylation art and need not be described here in great detail. It is important to emphasize that the nature of the alkylation process and catalyst is not critical to the success of our invention and is largely a matter of choice to be made by the practitioner.

The selective alkylation zone produces a selective alkylation zone effluent that enters separation facilities for the recovery of products and recyclable feed compounds. Suitable distillation facilities for such separations, which are well known by those skilled in the art and can be tailored as desired to provide specific fractions and purities, are described in U.S. Pat. Nos. 3,950,448; 4,237,327; 4,237,328; and 5,012,021. In one commonly employed arrangement, the bottoms stream of the HF stripping column where the alkylation catalyst is FIF, or the selective alkylation zone effluent stream where the alkylation catalyst is a solid alkylation catalyst, passes into a benzene column which produces an overhead stream containing benzene and a bottoms stream containing the alkylate product. This bottoms stream passes into a paraffin column which produces an overhead liquid stream containing unreacted paraffins, which normally is recycled as a recycle stream to the dehydrogenation zone, and a bottoms stream containing the product alkylate and any higher molecular weight side product hydrocarbons formed in the selective alkylation zone. This bottoms stream is passed into a rerun column which produces an overhead alkylate product stream containing the detergent alkylate and a bottoms stream containing polymerized olefins and polyalkylated benzenes (heavy alkylate).

A common variant of the subject process includes the selective hydrogenation of diolefins that are normally present in the dehydrogenated product stream or the stripping effluent stream. It is well known that diolefins are formed during the catalytic dehydrogenation of paraffins. Selective diolefin hydrogenation converts the diolefins to monoolefins, which are the desired product of the dehydrogenation section, and produces a selective diolefin hydrogenation product stream.

Another common variant of the subject process includes the selective hydrogenation of monoolefins that are normally present in the overhead liquid stream of the paraffin column. It is well known that unreacted monoolefins from the selective alkylation zone are present in the overhead liquid stream, and that these monoolefins shorten the life of currently available dehydrogenation catalysts where the overhead liquid stream is recycled to the dehydrogenation zone. Selective monoolefin hydrogenation converts the monoolefins to paraffins, which are the desired feed compound of the dehydrogenation section, and produces a selective monoolefin hydrogenation product stream.

We shall now describe the incorporation of an aromatic byproducts removal zone into this typical dehydrogenation-alkylation process. The aromatics byproducts removal zone eliminates or significantly reduces the aromatic byproducts in the feedstock to the selective alkylation zone in the prior art processes for the production of alkylated aromatic compounds. It reduces the deactivation rate of solid alkylation catalyst and, thereby, produces a significantly higher yield of linear alkylated aromatic compounds.

The aromatic byproducts removal zone selectively removes at least a portion of the aromatic byproducts in the dehydrogenated product stream using at least one aromatics removal zone. An aromatics removal zone may be placed in one or more locations in the process. The aromatic byproducts may be selectively removed from the dehydrogenated product stream and the stripping effluent stream. Also, where the subject process includes a selective diolefin hydrogenation zone, the aromatic byproducts may be selectively removed from the selective diolefin hydrogenation product stream. The aromatics removal zone is preferably located between the dehydrogenation zone and the selective alkylation zone because the aromatic byproducts are preferably selectively removed prior to entering the selective alkylation zone. These locations set forth above are not necessarily equivalent in terms of the required equipment, such as heaters, heat exchangers, vessels, coolers, and etc., to practice the process. Those skilled in the art of hydrocarbon processing are able to design and provide the required equipment.

Suitable aromatics removal zones may be selected from any processing methods that exhibit the primary requirement of selectivity for the aromatic byproducts. Suitable aromatics removal zones include, for example, sorptive separation zones and liquid-liquid extraction zones. However, it should be recognized that a particular aromatics removal zone may give better results than another zone. The preferred aromatics removal zone for use in the subject invention is a sorptive separation zone.

Where the aromatics removal zone is a sorptive separation zone, the removal of aromatic byproducts can be practiced in fixed bed or moving sorbent bed systems, but the fixed bed system is preferred. The sorbent may be installed in one or more vessels and in either series or parallel flow. The flow of the stream containing the aromatic byproducts through the sorptive separation zones is preferably performed in a parallel manner so that when one of the sorbent beds or chambers is spent by the accumulation of the aromatic byproducts thereon, the spent zone may be bypassed while continuing uninterrupted operation through the parallel zone. The spent zone of sorbent may then be regenerated or the spent sorbent may be replaced as desired.

The aromatic byproducts removal zone may also be practiced in a cocurrent, pulsed batch process, like that described in U.S. Pat. No. 4,159,284 or in a cocurrent, pulsed continuous process, like that disclosed in U.S. Pat. Nos. 4,402,832 and 4,478,721, both issued to Gerhold.

The aromatic byproducts removal zone may also be practiced in a countercurrent simulated moving bed system, such as described in U.S. Pat. No. 2,985,589 issued to Broughton. Cyclic advancement of the input and output streams can be accomplished by manifolding systems, which are also known, e.g., by rotary disc valves shown in U.S. Pat. Nos. 3,040,777 and 3,422,848. Equipment utilizing these principles arc familiar, in sizes ranging from pilot plant scale, such as described in U.S. Pat. No. 3,706,812 issued to deRosset, to commercial scale in flow rates from a few cc per hour to many thousands of gallons per hour.

Suitable sorbents may be selected from materials which exhibit the primary requirement of selectivity for the aromatic byproducts and which are otherwise convenient to use. Suitable sorbents include, for example, molecular sieves, silica, activated carbon, activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic byproducts, the selectivity of the sorbent to retain the aromatic byproducts which are more detrimental to solid alkylation catalysts, and the cost of the sorbent.

The preferred sorbent is a molecular sieve, and the preferred molecular sieve is 13X zeolite (sodium zeolite X). Detailed descriptions of zeolites may be found in the book authored by D. W. Breck entitled "Zeolite Molecular Sieves" published by John Wiley and Sons, New York, in 1974.

Those skilled in the art are able to select the appropriate conditions for operation of the sorbent without undue experimentation. For example, a fixed bed sorptive separation zone containing 13X zeolite may be maintained at a temperature from about 20° C. to about 300° C. and preferably from about 100° C. to about 200° C., a pressure effective to maintain the stream containing the aromatic byproducts in a liquid phase at the chosen temperature, and a liquid hourly space velocity from about 1 $hr^{-1}$ to about 10 $hr^{-1}$ and preferably from about 1 $hr^{-1}$ to about 3 $hr^{-1}$. The flow of the stream containing the aromatic byproducts through the sorptive separation zone may be conducted in an upflow, downflow or radial-flow manner.

Although both liquid and vapor phase operations can be used in many sorptive separation processes, liquid phase operation is preferred for the sorptive separation zone of our invention because of the lower temperature requirements and because of the higher sorption yields of the aromatic byproducts that can be obtained with liquid phase operation over those obtained with vapor phase operation. Therefore, the temperature and pressure of the sorptive separation zone during sorption of the aromatic byproducts are preferably selected to maintain in a liquid phase the stream from which the aromatic byproducts are selectively removed. Alternatively, the temperature and pressure of the sorptive separation zone during sorption of the aromatic byproducts can be selected to maintain in a liquid phase the aromatic byproducts in the stream from which the aromatic byproducts are selectively removed. Mixed phases (i.e., a combination of a liquid phase and a vapor phase) for the stream from which the aromatic byproducts are separated are generally not preferred because of the well-known difficulties involved in maintaining uniform flow distribution of both a liquid phase and a vapor phase through a sorptive separation zone. The operating conditions of a sorptive separation zone can be optimized by those skilled in the art to operate over wide ranges, which are expected to include the conditions in the reaction zones of our invention and its variants. Therefore, a sorptive separation zone may be contained in a common reaction vessel with the dehydrogenation zone, the selective diolefin hydrogenation zone, or the selective alkylation zone.

In general, during normal processing (i.e., during the sorption step), the effluent stream withdrawn from the aromatic byproducts removal zone has a lower molar ratio of aromatic byproducts per monoolefin, based on the total monoolefins in the effluent stream, than the molar ratio of aromatic byproducts per monoolefin of the stream from which the aromatic byproducts are removed, based on the total monoolefins in the stream which is passed to the aromatic byproducts removal zone. During the sorption step, the effluent stream's molar ratio of aromatic byproducts per monoolefin, based on the total monoolefins in the effluent stream, is generally less than 50%, preferably less than 20%, and more preferably less than 1%, of the molar ratio of aromatic byproducts per monoolefin of the stream which is passed to the aromatic byproducts removal zone, based on the total monoolefins in the stream which is passed to the aromatic byproducts removal zone. During sorption, the molar ratio of aromatic byproducts per monoolefin, based on the total monoolefins in the effluent stream, of the effluent stream is generally less than 0.2, and may be even lower.

Following an appropriate processing period, which will depend on the composition of the stream containing the aromatic byproducts and the particular aromatic byproducts themselves, it is usually necessary to regenerate the sorbent, that is to remove or desorb the sorbed aromatic byproducts from the sorbent so that the sorbent may be reused.

It should be understood that, prior to desorption or regeneration, it is also preferred to purge or displace from the void volume of the sorbent bed the unsorbed components of the stream from which the aromatic byproducts were removed. This is preferred because, when the aromatic byproducts are desorbed from the sorbent, they enter the void volume in the sorbent bed. If, at that time, that void volume contains unsorbed components, then desorption would have the adverse effect of re-contaminating the unsorbed components in the void volume with aromatic byproducts that are being desorbed. Clearly, this would be counter-productive and undesirable, since in effect it would partially undo some of the removal of aromatic byproducts that had been accomplished in the sorption step. Furthermore, the resulting contaminated mixture in the pore volume of the sorbent bed would not be readily separable by distillation, since the aromatic byproducts have boiling points in the same range as those of the unsorbed components in the void volume of the bed.

There are numerous methods of purging the sorbent bed. It is not intended to limit this invention to any particular method of purging the sorbent. Suitable purging methods include contacting the sorbent with a liquid, or with a vapor or gas, or with a mixture of a liquid and a vapor or gas, to displace or purge the unsorbed components from the sorbent. Suitable liquids may be selected from materials which exhibit the primary requirement of displacing or purging the unsorbed components from the sorbent without desorbing sorbed aromatic byproducts to an undesirable extent, and which are otherwise convenient to use. Suitable liquids include, for example, lighter paraffins and olefins, including $C_4$ to $C_9$ paraffins and olefins, preferably $C_5$ to $C_7$ paraffins and olefins, and more preferably $C_4$ to $C_6$ paraffins and olefins, and mixtures thereof. Suitable combinations of vapors or gases and liquids include a hydrogen-containing gas or vapor and a pentane-containing liquid. In a preferred method of regeneration, liquid n-pentane may be used.

Those skilled in the art are able to select the appropriate conditions for purging the sorbent without undue experimentation. For example, a fixed bed sorptive separation zone containing 13 X zeolite may be purged using a purge stream of 100 vol-% liquid n-pentane at purging conditions including a temperature from about 20° C. to about 300° C. and preferably from about 100° C. to about 200° C., a pressure of from atmospheric pressure to a pressure effective to maintain the n-pentane in a liquid phase at the chosen temperature, and a liquid hourly space velocity from about 1 $hr^{-1}$ to about 10 $hr^{-1}$ and preferably from about 1 $hr^{-1}$ to about 3 $hr^{-1}$. The flow direction of the purge stream through the sorptive separation zone may be upflow or radial flow, but the preferred direction is downflow. Relative to the flow direction of the stream passing through the sorbent bed during normal processing, the flow direction of the purging stream is preferably in the same direction, but it may be in any other direction, such as the opposite direction.

The purging step produces a purging effluent, whose composition usually changes during the course of the purging step as more and more of the unsorbed components are purged or displaced from the void volume of the sorbent bed. In a common arrangement, the sorbent bed is an elongated bed, the purge stream is introduced at one end of the sorbent bed, the purging effluent is withdrawn from an opposite or otherwise remote end of the bed, and the purge stream passes through the sorbent bed in a plug-flow manner from the inlet end to the outlet end. At the start of the purging step with this arrangement, the purging effluent contains mainly the unsorbed components, but at the end of the purging step the purging effluent contains mainly the components of the purge stream. Depending on the extent of backmixing within the sorbent bed during the purging step, this transition in the composition of the purging effluent may occur over a very short period of time or it may take place in a gradual, progressive fashion over the course of the purging step.

After the sorbent bed is purged, the sorbent bed is regenerated. There are numerous methods of regenerating or the sorbent, which is also referred to herein as desorption. It is not intended to limit this invention to any particular method of regenerating the sorbent. Suitable desorption methods include contacting the sorbent with a liquid, or with a vapor or gas, or with a mixture of a liquid and a vapor or gas, to displace or desorb the sorbed aromatic byproducts from the sorbent. Suitable liquids may be selected from materials that exhibit the primary requirement of displacing the aromatic byproducts from the sorbent in which are otherwise convenient to use. Suitable liquids include, for example, lighter (e.g., $C_6$–$C_8$) aromatics hydrocarbons including benzene and/or lighter paraffins and olefins, including $C_6$ to $C_9$ paraffins and olefins, and mixtures thereof. Suitable combinations of vapors or gases and liquids include a hydrogen-containing gas or vapor and a benzene-containing liquid. In a preferred method of regeneration, liquid benzene may be used.

Those skilled in the art are able to select the appropriate conditions for regeneration of the sorbent without undue experimentation. For example, a fixed bed sorptive separation zone containing 13 X zeolite may be regenerated using a desorbent stream of 100 vol-% liquid benzene at regeneration conditions including a temperature from about 20° C. to about 300° C. and preferably from about 100° C. to about 200° C., a pressure of from atmospheric pressure to a pressure effective to maintain the n-pentane in a liquid phase at the chosen temperature, and a liquid hourly space velocity from about 1 hr$^{-1}$ to about 10 hr$^{-1}$ and preferably from about 1 hr$^{-1}$ to about 3 hr$^{-1}$. The flow direction of the desorbent stream through the sorptive separation zone may be upflow or radial flow, but the preferred direction is downflow. Relative to the flow direction of the stream passing through the sorbent bed during normal processing, the flow direction of the desorbent stream is preferably in the same direction, but it may be in any other direction, such as the opposite direction.

The regeneration or desorption step produces a desorption effluent, whose composition usually changes during the course of the desorption step as more and more of the aromatic byproducts are removed or desorbed from the sorbent bed. In the arrangement described above of an elongated sorbent bed, at the start of the desorption step, the desorption effluent contains mainly the components of the purge stream, but at the end of the desorption step the purging effluent contains mainly the components of the desorbent stream. During the desorption step, the concentration of the aromatic byproducts in the desorption effluent varies, depending on how readily they are desorbed from the sorbent. For example, the concentration of aromatic byproducts in the desorption effluent may be low or nil at the start of desorption step, rise up to a peak or maximum during the middle of desorption when aromatic byproducts are being desorbed from a large portion of the sorbent bed, and drop down again at the end of the desorption step once most of the aromatic byproducts have been desorbed. Also, the composition of the desorption effluent may vary depending on the extent of backmixing within the sorbent bed during the desorption step.

Following the desorption period, the bed is usually in a suitable condition for reuse for sorbing aromatic byproducts from the stream that is normally being processed, such as the dehydrogenated product stream. However, it should be understood that in certain methods of regeneration it may also be necessary to remove the regenerating or desorbing medium from the sorbent before normal processing.

While the purging effluent usually contains unsorbed components of the stream from which the aromatic byproducts are removed, especially at the start of the purge step, the desorption effluent may contain none of these components. As more of the unsorbed components are displaced from the void volume in the sorbent bed during the purge step, less unsorbed components remain in the void volume at the start of the desorption or regeneration step. Thus, if the extent of purging of the unsorbed components from the void volume is substantially completed during the purge step, then little or no additional unsorbed components will be purged from the void volume when the desorbent stream is introduced. In that case, even at the start of the desorption step, the desorption effluent will contain very little of the unsorbed components. On the other hand, if the extent of purging of the void volume during the purge step is relatively slight, then the desorption effluent will contain relatively more of the unsorbed components. Thus, the concentration and quantity of unsorbed components in the desorption effluent depends on the extent of purging during the purge step. That extent of purging, in turn, is determined by balancing the cost of performing an extended or more complete purge with the benefit of recovering the unsorbed components in the purging effluent rather than in the desorption effluent. As will be illustrated hereinafter, essentially all of the unsorbed components that are recovered in the purging effluent are capable of being used productively to produce alkylaromatic product, since these unsorbed components are recovered in the sidedraw stream of the dividing wall distillation column and thus pass to the selective alkylation zone. On the other hand, essentially all of the unsorbed components that are recovered in the desorption effluent are lost from the process, since they are recovered in the bottom stream of the dividing wall distillation column and thus are rejected with the aromatic byproducts. A person of ordinary skill in the art can compute the benefits and costs of extending the purge step in order optimize the recovery of the unsorbed components.

The streams that are separated in the dividing wall distillation column that is used in the process of this invention are the purging effluent and the desorption effluent. The purging effluent is preferably a liquid phase mixture, but may be a two-phase, vapor-liquid mixture comprising from about 0 to about 70 mol-% vapor phase. The temperature of the purging effluent is generally from about 100 to about 275° F. (38 to 135° C.), and preferably from about 175 to about 185° F. (79 to 85° C.). The desorption effluent is also preferably a liquid phase mixture, but may be a two-phase, vapor-liquid mixture comprising from about 0 to about 20 mol-% vapor phase. The temperature of the desorption effluent is generally from about 200 to about 250° F. (93 to 121° C.), and preferably from about 230 to about 240° F. (110 to 115° C.).

The description that follows is written in terms of fractionating a purging effluent and a desorption effluent into a light or overhead stream comprising the purge component, a sidedraw or product stream comprising the desorbent component, and a heavy or bottom stream comprising the aromatic byproducts. The purge component generally has a lower boiling point than the desorbent component and typically contains at least one fewer carbon atom than the desorbent component. The aromatic byproducts generally have a higher boiling point than the desorbent component and typically contain at least four more carbon atoms than the desorbent component. The arrangement of the dividing wall distillation column and any associated equipment and its operating conditions (e.g., temperatures and vapor/liquid ratios) in the description that follows will be those generally associated with accomplishing such a separation in accordance with this invention, and are not intended to limit the scope of the invention as set forth in the claims.

The present invention is applicable to a wide variety of alkylaromatic processes using a dehydrogenation zone, a selective alkylation zone, and a sorptive aromatic byproducts removal zone, but the most widely practiced alkylaromatic process to which the present invention is applicable is one in which the paraffinic feed is $C_{10}$ to $C_{15}$ paraffin, the aromatic feed is benzene, the purge compound for purging the void volume of the sorbent beds in the aromatic byproducts removal zone is n-pentane, and the desorbent compound for desorbing or removing aromatic byproducts from the sorbent beds in the aromatic byproducts removal zone is benzene. Thus, a common example of a separation that can be accomplished using the subject invention is the separation of a purge stream comprising n-pentane and $C_{10}$ to $C_{15}$ paraffinic and olefinic hydrocarbons and a desorbent stream comprising benzene, aromatic byproducts, and pentane into a light stream comprising n-pentane, a sidedraw stream comprising benzene and $C_{10}$ to $C_{15}$ paraffinic and olefinic hydrocarbons, and a heavy stream comprising aromatic byproducts having from 10 to 15 carbon atoms. In this typical separation, the unsorbed components of the stream from which the aromatic byproducts are removed comprise $C_{10}$ to $C_{15}$ paraffins and olefins. The discussion of the invention described herein will be in reference to its application to this common separation. It is not intended that such discussion limit the scope of the invention as set forth in the claims.

Despite fluctuations in the compositions of the purging and desorbent effluents, unique requirements for the separation of co-boiling compounds into the sidedraw stream and the bottom stream, and a relatively tight specification on the aromatic byproducts in the sidedraw stream containing the desorbent compounds, it has now been recognized that, when producing LAB using an aromatic byproducts removal zone downstream of the dehydrogenation zone and upstream of the selective alkylation zone, two fully or non-fully thermally coupled distillation columns or a dividing wall distillation column is suitable for producing the desired fractions. Since the capital cost of a single new dividing wall distillation column is generally less than that of two new thermally coupled distillation columns, the use of a dividing wall distillation column will be described first, followed by a description of the use of two thermally coupled distillation columns.

When using a dividing wall distillation column, the desorbent component is withdrawn from the dividing wall distillation column in a sidedraw stream. The dividing wall distillation column also produces an overhead stream comprising the purge component and a bottom stream comprising the aromatic byproducts. The dividing wall distillation column has two inlets, one for each of the purge stream and the desorbent stream, and three outlets, one outlet for each of the overhead stream, the sidedraw stream, and the bottom stream.

The dividing wall distillation column has three distillation zones, a top zone, a middle zone, and a bottom zone. The middle zone contains at least one dividing wall, which is sometimes referred to herein as a partition, the plane of which is vertically oriented. As used herein, the phrase "vertically oriented" means forming an angle with the horizontal of generally between about 85 and about 95 degrees, and preferably between about 87.5 and 92.5 degrees. The longitudinal axis of the middle zone is also generally vertical, as are the longitudinal axes of the top and bottom zones. In the case of a single dividing wall, the dividing wall divides the middle zone into two portions, a feed-side portion and a sidedraw-side portion. Neglecting the areas occupied by the thickness of the dividing wall and the thickness of the column walls, the area of any horizontal cross-section of the column is thus divided between the feed-side portion and the sidedraw-side portion. The division of the column's horizontal cross-section between these two portions is not necessarily equal. The division depends on the composition of the feed and on the proportion of the feed that is in the vapor phase. The area of the feed-side portion is generally from about 30% to about 50%, and preferably from about 35% to about 45% of the area of any horizontal cross-section. Accordingly, the area of the sidedraw-side portion is generally from about 50% to about 70%, and preferably from about 55% to about 65% of the area of any horizontal cross-section. Multiple partitions or dividing walls may divide the middle zone into two or more portions.

Each partition or dividing wall is generally a baffle that is preferably imperforate. The dividing wall may be a single piece or may consist of multiple sectional pieces that are affixed together, such as by welding or bolting. The baffle is generally rectangular having two faces and four edges. One face of the baffle faces the feed-side portion of the middle zone, and the other face faces the sidedraw-side portion. The four edges are arranged in two pairs of generally opposing edges. One pair of edges comprises the side edges of the baffle, and each edge of this pair is affixed to the inside column wall of the middle zone. In case of a single baffle, each edge of this pair is sealingly engaged to the inside wall in a manner, such as by seal welding, so that with respect to passing between the attached edge and the column wall, fluids in one portion of the middle zone are not in communication with fluids in the other portion. Neither edge of the other pair of generally opposing edges is attached to the column wall. One of the edges of this other pair is the top edge of the dividing wall and delineates the top of the middle zone and the bottom of the top zone. The other edge is the bottom edge of the dividing wall and delineates the bottom of the middle zone and the top of the bottom zone. None of the four edges is necessarily straight. For example, depending on the contour of the column wall, the side edges may be shaped or rounded in order to facilitate attachment of the dividing wall to the column wall. Also, the top edge may be shaped or segmented in a manner that facilitates attachment or fit-up between the dividing wall and plates or other column internals in the top of the middle zone and/or the bottom of the top zone. Likewise, the bottom edge may be shaped to enhance the fit between the dividing wall and plates or internals at the bottom of the middle zone and/or the top of the bottom zone.

The thickness of the dividing wall may be any suitable thickness, subject to mechanical requirements of the structural strength of the dividing wall, attachment to the column wall, or attachment to other column internals. The thickness of the dividing wall depends on the column diameter, but is usually between 3/8 in and 3/4 in (9.5 and 19.1 mm) for column diameters between 6 ft and 36 ft (1.8 and 11.0 m). The dividing wall may comprise two walls with a gas space in between, such as disclosed in U.S. Pat. No. 5,785,819. The dividing wall may be constructed from any suitable material, and it is believed preferable that the dividing wall and the column wall shell are of the same material. The dividing wall material is usually carbon steel. The surfaces of the faces of the dividing wall are generally smooth. However, either surface may have liquid deflectors, such as disclosed in U.S. Pat. No. 5,785,819.

Vapor-liquid contacting devices are installed on the feed-side portion and the sidedraw-side portions in the middle zone of the dividing wall distillation column. Any suitable vapor-liquid contacting device may be used. Suitable vapor-liquid contacting devices, including plates and packing, and their performances are described at pages 14–24 to 14–61 of *Perry's Chemical Engineers' Handbook*, $7^{th}$ Edition, edited by D. W. Green et al., published by McGraw-Hill, New York, in 1997. As used herein, the term "plate" includes tray, and suitable trays include those formed from a number of adjacent triangular (v-shaped) downcomers or other multiple downcomers, which are disclosed in U.S. Pat. Nos. 5,262,094, 5,366,666, 5,407,605, 5,554,329, and 5,707,563, the teachings of all of which are incorporated herein by reference. A bed-like layer of packing material may be closely adjacent to the bottom surface of the plate in the so-called "disengagement" zone under the plate. The packing may extend to the plate below.

In the feed-side portion, generally from about 3 to about 8 or more plates, and more typically from about 4 to about 6 plates, are located above the elevation of the desorption effluent inlet and below the elevation of the top edge of the dividing wall, with generally from about 10 to about 20 or more plates, and more typically from about 14 to about 15 plates, located between the desorption effluent inlet and the bottom of the dividing wall. In the sidedraw-side portion, generally from about 10 to about 20 or more plates, and more typically from about 14 to about 15 plates, are located above the sidedraw outlet and below the top edge of the dividing wall, while generally from about 3 to about 8 or more plates, and more typically from about 4 to about 6 plates, are located between the sidedraw outlet and the bottom of the dividing wall. Plate spacings in part or parts of the feed-side portion may be the same as or different from not only plate spacings in part or parts of the sidedraw-side portion but also spacings in other part or parts of the feed-side portion. Generally, the spacings for the feed plate and the sidedraw plate are generally greater than spacings for other plates. The plates referred to in this paragraph are assumed to have a plate efficiency of 80%. As used herein, plate efficiency is the approach to equilibrium defined as the ratio of the actual change in vapor composition as the vapor passes through the plate to the change that would have occurred if the vapor had reached a state of equilibrium with the liquid leaving the plate. If plates having a plate efficiency other than 80% are used, a person of ordinary skill in the art of distillation is able to readily determine the appropriate number of plates.

In the sidedraw-side portion, the sidedraw is withdrawn from a downcomer into which liquid flows, preferably from an accumulator plate. As used herein, the term "accumulator plate" generally refers to a plate on which downflowing liquid can collect and through which upflowing vapor can pass, but nevertheless on which no substantial vapor-liquid contacting or distillation occurs. Even though an inventory of liquid may collect on the upper side of the accumulator plate, upflowing vapors passing from the under side to the upper side of the accumulator plate do not pass through or contact that liquid to any significant extent, because the vapors pass through channels which discharge the vapors on the top side of the accumulator plate at an elevation that is above the surface of the accumulated liquid. Having in effect bypassed the liquid on the accumulator plate, these vapors then flow upward to the under side of the next higher plate in the column. Referring now to the particular accumulator tray that is preferably used for the sidedraw, at least a portion of the liquid that collects on the accumulator plate preferably flows to a downcomer from which the liquid is in turn withdrawn from the dividing wall distillation column. Preferably both the accumulator plate and the downcomer ensure that essentially none of the liquid that collects on the accumulator plate or in the downcomer passes downward to the plate below the accumulator plate. That is, preferably all or essentially all of the liquid that collects on the accumulator plate or in the downcomer is withdrawn from the column. As used herein, the term "essentially none" means generally less than 5% and preferably less than 1%, and the term "essentially all" means generally more than 95% and preferably more than 99%. In this way, essentially all of the unsorbed components that were present in the stream from which the aromatic byproducts were removed and that enter the column with the purging effluent are recovered in the sidedraw stream rather than in the bottom stream, where they would be rejected from the process. In those embodiments of this invention where little or none of the liquid flowing downward in the sidedraw-side of the column passes below the sidedraw accumulator plate, a liquid stream is preferably introduced into the sidedraw-side of the column at a point directly below the sidedraw accumulator plate. This liquid stream in effect provides reflux for plates located on the sidedraw-side of the column and below the sidedraw accumulator plate. This liquid stream preferably has a low concentration of the unsorbed components of the stream from which the aromatics byproducts are removed.

Vapor-liquid contacting devices are also installed in the top zone of the dividing wall distillation column, and any of the previously-mentioned gas-liquid contacting devices are suitable for the top zone. In the top zone, generally from about 8 to about 20 plates, and more typically from about 14 to about 15 plates, are located above the elevation of the purging effluent inlet, with generally from about 5 to about 15 plates, and more typically from about 9 to about 10 plates, located between the purging effluent inlet and the top of the dividing wall. The plates referred to in this paragraph are assumed to have a plate efficiency of 80%. Usually, the spacing between plates is generally uniform in the top zone, but is not necessarily the same as in the middle zone or the bottom zone. In the top zone, an accumulator plate is preferably used to collect liquid that passes downward through the bottom-most gas-liquid contacting plate in the top zone. This accumulator plate preferably ensures that essentially none of the liquid that collects on it passes downward to the feed-side portion of the middle zone. In this way, essentially all of the unsorbed components that enter the dividing wall distillation column with the purging effluent are directed to the sidedraw-side portion of the middle zone, so that they may be recovered in the sidedraw stream rather than in the bottom stream. In those embodiments of this invention where the liquid flowing downward from the top zone to the feed-side portion is insufficient to provide the required quantity of reflux on the feed-side portion above the desorption effluent inlet, a liquid stream is preferably introduced into the sidedraw-side of the column at a point directly below the top zone accumulator plate. Usually, this liquid stream is introduced to the uppermost plate on the feed-side portion. This liquid stream in effect provides reflux for plates located on the feed-side portion of the column. This liquid stream preferably has a low concentration of the unsorbed components of the stream from which the aromatics byproducts are removed.

Vapor-liquid contacting devices are also installed in the bottom zone of the dividing wall distillation column, and any of the previously-mentioned gas-liquid contacting devices are suitable for the bottom zone. In the bottom zone, it may be to preferable to locate an accumulator plate above the uppermost gas-liquid contacting plate in the lower zone. At that location, an accumulator plate could collect the two downflowing liquids that exit the bottom of the middle zone, namely the liquids exiting from the bottom of the feed-side and sidedraw-side portions. These liquids preferably would mix together on the accumulator plate in order to help ensure a is relatively uniform composition of the liquid that flows from the accumulator plate to the gas-liquid contacting plates in the bottom zone. In addition, the liquid discharge or downcomer of the accumulator plate would be oriented to ensure that liquid falling from the accumulator plate would undergo efficient vapor-liquid contacting on the uppermost fractionating plate in the bottom zone. The bottom zone contains generally from about 10 to about 25 plates, and more typically from about 15 to about 20 plates. The plates referred to in this paragraph are assumed to have a plate efficiency of 50–80%. Usually, the spacing between plates is generally uniform in the bottom zone, but is not necessarily the same in both the top and bottom zones.

Persons of ordinary skill in the art of distillation are aware that, with all other variables constant, the number of plates in a distillation zone generally varies directly with the V/L ratio. As used herein, the V/L ratio, or simply V/L, is the ratio of moles of upflowing vapor (V) to moles of downflowing liquid (L). The designer of a distillation zone arrives at the optimum number of plates and the optimum V/L ratio by trading-off or balancing the capital cost of the distillation column on the one hand with the operating cost on the other hand. To achieve a given separation, the higher the V/L, the greater is the number of plates. This relationship applies within the dividing wall distillation column to each of the top, middle, and bottom zones; within the top zone to the plates above and below the purging effluent inlet; within the middle zone to both the feed-side portion and sidedraw-side portions; within the feed-side portion to the plates above the desorption effluent inlet and to those below the feed inlet; and within the sidedraw-side portion to the plates above the sidedraw outlet and to plates below the sidedraw outlet. Accordingly, a person of ordinary skill in the art is aware that the number of plates in a zone, portion, or part of a portion of the dividing wall distillation column may be more than or less than the numbers of plates set forth above, depending on the V/L in that respective zone, portion, or part of a portion of the column. Where packing is used in a zone, either in addition to or instead of plates, such a zone is usually designed based on the hydraulic performance (e.g., pressure drop, flooding, and loading) and mass transfer performance (e.g., height equivalent to a theoretical plate, or HETP).

The plates above the desorption effluent inlet in the feed-side portion function as a rectification section to decrease the concentration of aromatic byproducts, without significantly decreasing the concentration of the purge compound (n-pentane) in the upflowing vapor. It is believed that a substantial portion of the aromatic byproducts that are present in the sidedraw stream are high-boiling hydrocarbons that flow upward in the feed-side portion, reach the top of the dividing wall, flow downward through the plates in the sidedraw-side portion, and ultimately exit in the sidedraw stream. Accordingly, the molar ratio V/L in the feed-side portion above the feed inlet, as well as the temperature at the top of the dividing wall in the feed-side portion, are important parameters for controlling the concentration of aromatic byproducts in the sidedraw stream. In the feed-side portion above the feed inlet, V/L is generally from about 6 to about 8.

In the top zone, the plates above purging effluent inlet function as a rectification zone to decrease the concentration of the $C_{10}$–$C_{15}$ paraffins and olefins that enter the dividing wall distillation column with the purging effluent. These plates also help decrease the concentration of the desorbent component (e.g., benzene) in the upflowing vapor in order to attain a highly concentrated overhead stream comprising n-pentane. V/L in the top zone above the purging effluent inlet is generally from about 1.0 to about 2.2. The plates below the purging effluent inlet in the top zone act as a stripping section to decrease the concentration of n-pentane in the downflowing liquid without significant decreasing the concentrations of benzene and $C_{10}$–$C_{15}$ paraffins and olefins. V/L in the top zone below the purging effluent inlet is generally from about 0.5 to about 1.6.

The plates below the desorption effluent inlet in the feed-side portion act as a stripping section to decrease the concentration of n-pentane without significantly decreasing the concentrations of aromatic byproducts and $C_{10}$–$C_{15}$ paraffins and olefins in the downflowing liquid. It is believed that a substantial portion of the n-pentane that is present in the sidedraw stream is n-pentane that flows downward in the feed-side portion, reaches the bottom of the dividing wall, and flow upward through the sidedraw-side portion, and ultimately exit in the sidedraw stream. Accordingly, the V/L in the feed-side portion below the desorption effluent inlet, as well as the temperature at the bottom of the dividing wall in the feed-side portion, are important parameters for controlling the concentration of n-pentane in the sidedraw stream. In the feed-side portion below the feed inlet, V/L is generally from about 0.25 to about 0.5.

The plates in the bottom zone act as a stripping zone not only to further decrease the concentration of n-pentane but also to decrease the concentration of benzene in the downflowing liquid in order to attain a highly concentrated bottom stream comprising aromatic byproducts and a minimal amount, if any, of $C_{10}$–$C_{15}$ paraffins and olefins. In the bottom zone, V/L is generally from about 0.6 to about 2.0.

The plates above the sidedraw outlet in the sidedraw-side portion act as a stripping section to decrease the concentration of n-pentane in the descending liquid. Although not a substantial portion of the n-pentane that is charged to the column with the purging effluent or the desorption effluent is present in the sidedraw stream, n-pentane that flows downward in the sidedraw-side portion above the sidedraw outlet can ultimately exit in the sidedraw stream. The V/L above the sidedraw outlet in the sidedraw-side portion is generally from about 0.4 to about 1.0.

The plates below the sidedraw outlet in the sidedraw-side portion act as a rectification section to decrease the concentration of aromatic byproducts in the ascending vapor. Although not a substantial portion of the aromatic byproducts that enter the column in the desorption effluent are present in the sidedraw stream, aromatic byproducts that flow upward in sidedraw-side portion below the sidedraw outlet can ultimately exit in the sidedraw stream. The V/L below the sidedraw outlet in the sidedraw-side portion is generally from about 3.0 to about 6.0.

The sidedraw stream is highly concentrated in benzene. The concentration in the sidedraw stream of hydrocarbons lighter than benzene, including n-pentane, is generally less than 2.5 wt-% and preferably less than 500 wt-ppm. The concentration in the sidedraw stream of aromatic byproducts is generally less than 0.5 wt-% and preferably less than 500 wt-ppm. As used herein, the term "recovery" of a component is computed by dividing the quantity of that component recovered from the dividing wall distillation column in one of the overhead stream, sidedraw stream, or bottom stream by the quantity of that component charged to the dividing wall distillation column in one or more of the desorption and purging effluents, and multiplying by 100. If the engineering units of quantity in the numerator and the denominator are the same, then recovery is dimensionless and is expressed as a percent. The recovery in the overhead stream of n-pentane that entered with the purging and desorption effluents is generally greater than 85% and preferably greater than 90%. The recovery in the sidedraw stream of benzene that entered with the purging and desorption effluents is generally greater than 85%, preferably greater than 90%, and even more preferably greater than 99.0%. The recovery in the sidedraw stream of $C_{10}$–$C_{15}$ paraffins and olefins that entered with the purging effluent is generally greater than 85%, preferably greater than 90% and even more preferably greater than 99.0%. Finally, the recovery in the bottom stream of aromatic byproducts that entered with the desorption effluent is generally greater than 85% and preferably greater than 90%.

At least a portion of the overhead stream from the dividing wall distillation column passes to an overhead condenser, which may be a partial condenser or a total condenser. The outlet of the overhead condenser passes to an overhead receiver, which separates the condensed material from any uncondensed overhead materials. At least a portion of the condensed overhead material is refluxed to the dividing wall distillation column, preferably to a point above the top plate in the top zone. The net overhead stream from the dividing wall distillation column may be comprise uncondensed material, condensed material, or a combination of uncondensed and condensed material from the overhead stream.

The overhead condenser may be a contact condenser. In a contact condenser, the condensing medium directly contacts the stream being condensed usually over a vapor-liquid contacting device, such as packing or any of the previously-mentioned gas-liquid contacting devices. Although the contact condenser may be external to the column, preferably the contact condenser is located within the column, and usually above the uppermost plate of the top zone. Vapors rising from the uppermost plate of the top zone pass upwardly through the contact condenser and countercurrently to the downward flow of the cooling medium. A net stream of uncondensed vapor is withdrawn from the top of the contact condenser and sent to recovery facilities. A liquid stream comprising condensing medium and condensed vapors is withdrawn from the bottom of the contact condenser. A portion of the liquid stream is withdrawn as a net stream from the bottom of the contact condenser and sent to recovery facilities, and the remaining portion is cooled and recycled to the top of the contact condenser. The contacting medium can comprise the low-boiling hydrocarbons or a portion of the overhead liquid of the distillation column that is recycled to the distillation column. The use of a contact condenser is advantageous because the pressure drop for the stream being condensed across a contact condenser is small relative to that across other condensers, which in turn allows the dividing wall distillation column to operate at a lower pressure.

At least a portion of the bottom stream from the dividing wall distillation column passes to a reboiler. The reboiler may be an external reboiler or an internal reboiler. A pump may be used to pass the portion of the bottom stream through the reboiler. Alternatively, the reboiler may be a so-called thermal siphon reboiler, in which reboiling changes the density of the material being reboiled and that density change, in turn, induces flow through the reboiler. The outlet stream of the reboiler is generally a two-phase mixture of vaporized material from the bottom stream and unvaporized material. At least a portion of the outlet stream of the reboiler passes to the dividing wall distillation column, preferably to a point below the bottom plate in the bottom zone. The net bottom stream from the dividing wall distillation column is generally withdrawn as a portion of the bottom stream prior to passing to the reboiler.

The dividing wall distillation column may also have one or more reboilers, where each reboiler is located at an elevation above that of at least one of the plates in the bottom zone. Such a reboiler, if any, is generally in addition to, rather than instead of, the reboiler to which the bottom stream from the dividing wall distillation column passes. Although such a reboiler, if any, may be located at an elevation above the bottom of the dividing wall, it is generally located below the bottom of the dividing wall. Although any such additional reboiler may be an external reboiler, preferably it is an internal reboiler, such as a stab-in reboiler.

The operating pressure of the dividing wall distillation column may be any suitable pressure at which the relative volatilities of the hydrocarbons to be separated are sufficiently different that the desired separation can be effected by distillation. The operating pressure is generally from about 35 to about 50 psi(a) (240 to 345 kPa(a)). It is believed that, within this operating pressure range, the lower the operating pressure, the lower will be the capital and operating costs of the dividing wall distillation column.

When using two thermally coupled distillation columns, whether fully thermally coupled or not, the desorption effluent passes to a prefractionator, the purging effluent passes to the main column, and three streams are withdrawn recovered from the main column: an overhead stream comprising n-pentane, a sidedraw stream comprising benzene, and a bottom stream comprising aromatic byproducts.

As used herein, two distillation columns are said to be thermally coupled if at least part of the heat transfer that is used for separation in the first column is provided by directly contacting the material being fractionated in the first column with a product stream from the second column. Direct contacting occurs when fluids withdrawn from a location inside the second column (e.g., from a plate, downcomer, packing, liquid sump, vapor space, etc.) are introduced into a location where fluids are present in the first column (e.g., into a plate, downcomer, packing, liquid sump, or vapor space), without first passing through a heat exchanger, such as a condenser or a reboiler. The phrase "without first passing through a heat exchanger" means that the heat content of the fluids entering the first column is generally from 95% to 105%, preferably from 99% to 101%, and more preferably from 99.5 to 100.5%, of the heat content of the fluids withdrawn from the second column. In practice, passing fluid from the second column to the first column results in the transfer of a small amount of heat between the fluid and the ambient surroundings, even if the fluid does not pass through a heat exchanger and even if the fluids are passed through a well-insulated conduit or line. The amount of heat exchanged between the fluid and the ambient surroundings is generally less than 5%, preferably less than 1%, and more preferably less than 0.5%, of the heat content of the fluids.

In a common arrangement of two thermally coupled distillation columns, instead of each column functioning as a "stand-alone" column with its own reboiler, a vapor stream from a plate (or a downcomer, packing, vapor space, etc.) inside the first column passes through a conduit to the bottom of the second column, and the liquid stream from the bottom of the second column passes through a conduit to a plate (or a downcomer, packing, sump, vapor space, etc.) inside the first column. Thus, the reboiler of the first column provides the reboiling duty for not only the first column but also the second column, and the second column does not have its own reboiler. In another common arrangement, a liquid stream from a plate (or a downcomer, packing, sump, etc.) inside the first column passes through a conduit to the top of the second column, and the vapor stream from the top of the second column passes through a conduit to a plate (or downcomer, packing, sump, vapor space, etc.) inside the first column. In this arrangement, the condenser of the first column provides the condensing duty for the first as well as the second column, and the second column does not have its "own" condenser. Examples of such thermally coupled distillation columns are shown in FIGS. 2(a) and 2(b) of the above-mentioned article by C. Triantafyllou and R. Smith, in Trans IChemE, Vol. 70, Part A, Mar. 1992, 118–132.

FIG. 2(c) of the article by C. Triantafyllou and R. Smith shows an arrangement of two thermally coupled distillation columns that are said to be fully thermally coupled, since one of the columns (the prefractionator) has neither its own condenser nor its own reboiler and the other column (the main column) has both a condenser and a reboiler. The condenser and reboiler of the main column provide the condensing duty and reboiling duty, respectively, not only for the main column but also for the prefractionator. Thus, the vapor stream from the top of the prefractionator passes through a conduit to a plate inside the main column, and a liquid stream from a plate inside the main column passes through a conduit to the top of the prefractionator. Also, the liquid stream from the bottom of the prefractionator passes through a conduit to a plate inside the main column, and a vapor stream from a plate inside the main column passes through a conduit to the bottom of the prefractionator. See also the article by H. Rudd in The Chemical Engineer, Distillation Supplement, August 27, 1992, s14–s15.

When using two fully thermally coupled distillation columns, the prefractionator separates the desorption effluent into a prefractionator overhead vapor stream and a prefractionator bottom liquid stream. In the prefractionator above the desorption effluent inlet, the plates act as a rectification section to decrease the concentration of aromatic byproducts in the upflowing vapor. There are generally from about 3 to about 8 or more plates, and more typically from about 4 to about 6 plates, above the elevation of the desorption effluent inlet, and the V/L ratio is generally from about 6 to about 10. In the prefractionator, below the elevation of the desorption effluent inlet, the plates act as a stripping section to decrease the concentration of n-pentane without significantly decreasing the concentration of aromatic byproducts in the downflowing liquid. There are generally from about 10 to about 20 or more plates, and more typically from about 14 to about 15 plates, and V/L is generally from about 0.25 to about 0.5 below the elevation of the desorption effluent inlet to the prefractionator. The plates referred to in this paragraph are assumed to have a plate efficiency of 80%. The vapor-liquid contacting devices previously described for use in the dividing wall distillation column are suitable for use in the prefractionator.

In the main column, the plates above the elevation where the purging effluent is introduced help to decrease the concentration of $C_{10}$–$C_{15}$ paraffins and olefins and to decrease the concentration of benzene in the upflowing vapors. In this part of the main column, there are generally from about 8 to about 20 or more plates, and more typically from about 14 to about 15 plates, and V/L is generally from about 1 to about 2.2. Below the elevation where the purging effluent is introduced and above the elevation where the prefractionator overhead vapor stream is introduced and the liquid stream from the main column is withdrawn for the prefractionator, the plates act as a stripping section to decrease the concentration of n-pentane in the descending liquid without significantly decreasing the concentrations of benzene and $C_{10}$–$C_{15}$ paraffins and olefins. There are generally from about 5 to about 15 or more plates, and typically from about 9 to about 10 plates, in this area of the main column, and V/L is generally from about 0.5 to about 1.6. Below the elevation where the prefractionator overhead vapor is introduced and the liquid stream from the main column is withdrawn for the prefractionator and above the elevation where the sidedraw stream is withdrawn, the plates act as a stripping section to decrease the concentration of n-pentane from the descending liquid. There are generally from 10 to about 20 or more plates, and typically from about 14 to about 15 plates, in this area of the main column, and V/L is generally from about 0.4 to about 1.0. The area of the main column below the elevation where the sidedraw stream is withdraw and above the elevation where the vapor stream from the main column is withdrawn and the prefractionator bottom liquid stream is introduced acts as a rectification section to decrease the concentration of aromatic byproducts in the ascending vapors. This area of the main column generally contains from about 3 to about 8 or more plates, and usually from about 4 to about 6 plates, and V/L is generally from about 3.0 to about 6.0. In the main column below the elevation where the vapor stream from the main column is withdrawn and the prefractionator bottom liquid stream is introduced, there are generally from about 10 to about 25 or more plates, and typically from about 15 to about 20 plates. This area of the main column acts as a stripping zone to decrease the concentrations of n-pentane and benzene, and V/L is generally from about 0.6 to about 2.0. The plates referred to in this paragraph are assumed to have a plate efficiency of 80%. Any suitable plate spacing(s) may be used in the main column. The vapor-liquid contacting devices previously described for use in the dividing wall distillation column are suitable for use in the main column. In a manner similar to that described previously for the dividing wall distillation column, a person of ordinary skill in the art of distillation can determine optimum numbers of plates and optimum V/L ratios for the main column, as well for in the prefractionator column.

In a preferred embodiment of this invention, the prefractionator and the main column are thermally coupled distillation columns but are not fully thermally coupled distillation columns, because a liquid stream from the main column is not withdrawn for the prefractionator. Instead, all or essentially all of the liquid that flows downward in the main column at the elevation where the prefractionator overhead vapor stream is introduced continues flowing downward in the main column. In this way, any $C_{10}$–$C_{15}$ paraffins and olefins in that downflowing liquid are not withdrawn and introduced into the prefractionator, but instead remain in the main column. In this way, the unsorbed components that were present in the stream from which the aromatic byproducts were removed and that enter the main column with the purging effluent are recovered in the sidedraw stream rather than in the bottom stream, where they would be rejected from the process. In those embodiments of this invention where little or none of the liquid flowing downward in the main column passes to the prefractionator, a liquid stream is preferably introduced into the prefractionator at an elevation above the top prefractionator plate. This liquid stream in effect provides reflux for plates located in the prefractionator. This liquid stream preferably has a low concentration of the unsorbed components of the stream from which the aromatics byproducts are removed.

In another preferred embodiment, the sidedraw is withdrawn from the main column via a downcomer into which liquid flows, preferably from an accumulator plate. More preferably, both the accumulator plate and the downcomer prevent any of the liquid that collects on the accumulator plate or in the downcomer from passing downward to the plate below the accumulator plate. By collecting and withdrawing all of the downflowing liquid at the sidedraw, essentially all of the unsorbed components that were present in the stream from which the aromatic byproducts were removed and that were flowing downward in the main column above the sidedraw are recovered in the sidedraw stream rather than in the bottom stream, where they would be rejected from the process. In this embodiment, a liquid stream is preferably introduced into the main column at a point directly below the sidedraw accumulator plate to effectively provide reflux for plates located below the sidedraw accumulator plate. This liquid stream preferably has a low concentration of the unsorbed components of the stream from which the aromatics byproducts are removed.

When using two thermally coupled distillation columns such as described above that are not fully thermally coupled, the composition of the sidedraw stream withdrawn from main column is generally the same as that already described for the sidedraw stream withdrawn from the dividing wall distillation column. In addition to producing a sidedraw stream, the main column also produces a net overhead stream and a net bottom stream. The composition of the main column's net overhead stream is generally the same as that described previously for the net overhead stream of the dividing wall distillation column, and the composition of the main column's net bottom stream is generally the same as that described previously for the net bottom stream of the dividing wall distillation column.

Regardless whether the sidedraw stream is produced by a dividing wall distillation column or by two thermally coupled distillation columns, whether fully thermally coupled or not, the sidedraw stream generally passes to a selective alkylation zone, as described previously. The effluent recovered from the selective alkylation zone usually passes to a product recovery section, which generally comprises at least three columns. The first column, or benzene column, separates the reactor effluent and removes unreacted aromatic compound reactant (e.g., benzene) as an overhead stream for recycle to, for example, the selective alkylation zone. The second, or paraffin, column removes paraffins from a bottom stream of the benzene column and produces a paraffin-containing overhead stream for recycle to the paraffin dehydrogenation zone. The third, or LAB, column separates a bottom stream from the paraffin column and produces an overhead stream containing LAB, which is recovered as product. Heavy alkylate is recovered as a bottom stream from the LAB column and may be further separated in a fourth column to recover any LAB present in the LAB column bottom stream.

Figure 2:
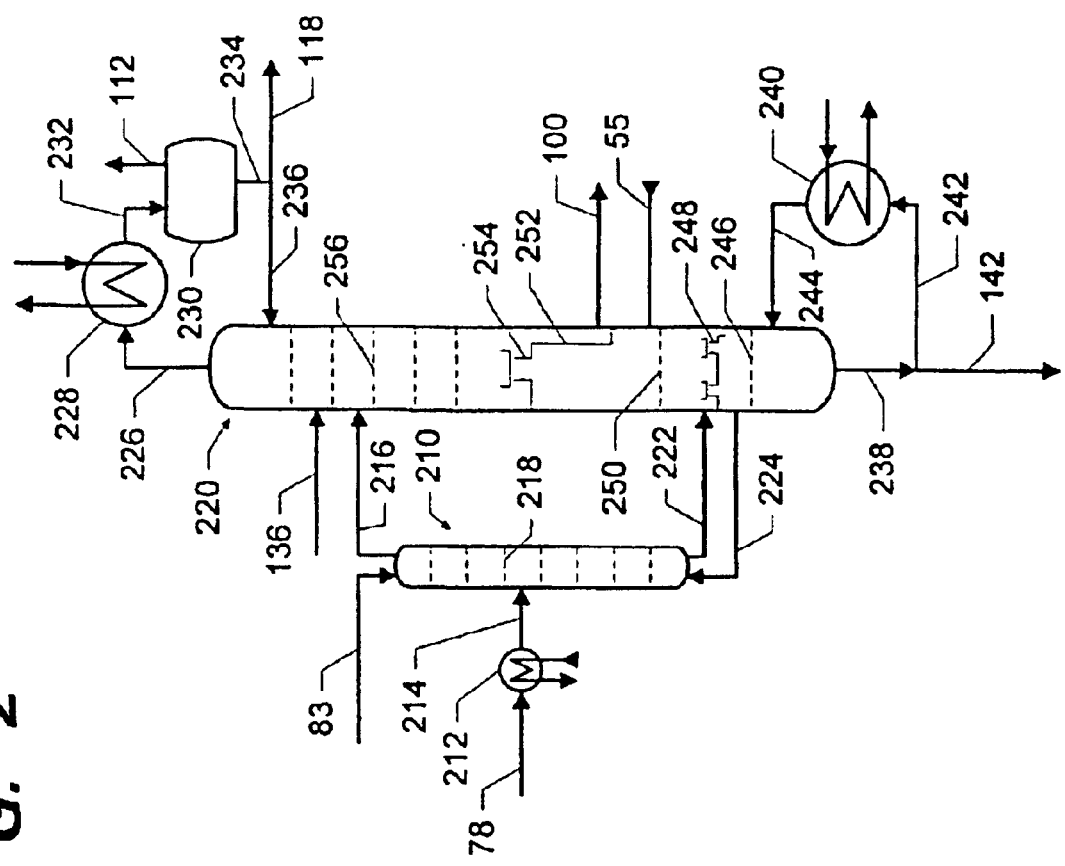

FIGS. 1 and 2 each illustrate a preferred embodiment of the subject invention. FIGS. 1 and 2 are presented solely for purposes of illustration and are not intended to limit the scope of the invention as set forth in the claims. FIGS. 1 and 2 show only the equipment and lines necessary for an understanding of the invention and does not show equipment such as pumps, compressors, heat exchangers, and valves which are not necessary for an understanding of the invention and which are well known to persons of ordinary skill in the art of hydrocarbon processing.

FIG. 1 depicts three sorbent-containing beds, 20, 120, and 70. Each sorbent bed is performing a different function. Sorbent bed 20 is on-stream and functions to remove aromatic byproducts from a dehydrogenated product stream flowing in line 14. Sorbent bed 120 is off-stream and its void volume is being purged by a purging stream containing n-pentane that flows in line 118. Sorbent bed 70 is also off-stream and aromatic byproducts on its sorbent are being desorbed by a desorbent stream containing benzene which flows in line 64. Each sorbent bed is shown with an inlet valve and an inlet line (16 and 18 for bed 20, 122 and 124 for bed 120, and 66 and 68 for bed 70, respectively), and an outlet line and an outlet valve (22 and 24 for bed 20, 126 and 128 for bed 120, and 72 and 74 for bed 70, respectively). The depicted arrangement of the inlet and outlet valves and lines of the beds permits the inlet and outlet of each bed to be closed, so that, using other additional valves and lines which are not shown but which a person of ordinary skill in the art can provide, the function of each bed can be periodically shifted to function as that of one of the other two beds in FIG. 1. Thus, in addition to being capable of functioning for sorption as shown in FIG. 1, on-stream bed 20 is also capable of functioning in the position shown in FIG. 1 for either off-stream bed 120 (purging) or off-stream bed 70 (desorption). Similarly, off-stream bed 120 is also capable of functioning in the position shown for either on-stream bed 20 or off-stream bed 70, and off-stream bed 70 is also capable of functioning in the position shown for either on-stream bed 20 or off-stream bed 120. Accordingly, in normal operation, the on-stream bed 20 and off-stream beds 120 and 70 can be periodically shifted, so that on-stream bed 20 functions as off-stream bed 120, off-stream bed 120 functions as off-stream bed 70, and off-stream bed 70 functions as on-stream bed 20. Additional beds (not shown) may also be available for functioning in the positions shown for any of beds 20, 120, and 70. The number of beds required to operate the process depends on many factors, including the duration of the sorption, purging, and desorption functions; the desired extent of removal of aromatics byproducts during sorption; the desired recovery of paraffins and olefins during purging; and capital and operating costs. However, a person of ordinary skill in the art can readily determine the optimum number of beds required to meet the desired objectives. In general, however, at least one sorbent bed is required, since even a single bed can function first in the position of bed 20, then in the position of bed 120, and finally in the position of bed 70, before functioning once again in the position of bed 20. More commonly, two or more beds are used, so that, as shown in FIG. 1, while one bed is functioning in the position of bed 20, other beds are functioning in the positions of beds 120 and 70. By shifting of the functions of one or more beds, the removal of aromatic byproducts from the dehydrogenated product stream can range from a batchwise operation with relatively long interruptions between periods of removal to an essentially continues operation, although in practice the removal may even then be semi-continuous due to short but finite times required for shifting functions. Likewise, the purging and desorption functions may occur batchwise and relatively infrequently or essentially continuously.

Referring now to FIG. 1, a paraffin feed stream comprising an admixture of $C_{10}$–$C_{15}$ is normal and branched paraffins is charged via line 10. The paraffin feed stream is usually obtained in part from the product of a paraffin adsorptive separation zone and in part from recycled paraffins recovered from the stream in line 34, although the adsorptive separation zone, the recovery of paraffins from stream 34, and the combination of these two sources of paraffins is not shown in FIG. 1. The paraffins enter dehydrogenation zone 12, where the paraffins are contacted with a dehydrogenation catalyst in the presence of hydrogen at conditions that effect the conversion of a significant amount of the paraffins to the corresponding olefins. Some aromatic byproducts are formed, and some diolefins may also be formed. A dehydrogenated product stream containing unreacted paraffins, monoolefins, and aromatic byproducts passes through line 14, valve 16, and line 18, and enters bed 20, which is on-stream for removal of aromatic byproducts. On-stream bed 20 contains a molecular sieve sorbent, which sorbs aromatic byproducts and removes them from the dehydrogenated product stream. The effluent of on-stream bed 20 passes through line 22, valve 24, and line 26, and enters selective alkylation zone 28, where monoolefins alkylate benzene to produce alkylbenzenes. Benzene for the alkylation reaction enters selective alkylation zone 28 in a stream that flows through line 58 and which contains not only benzene but also $C_{10}$–$C_{15}$ paraffins and n-pentane, and possibly a minor amount of water. An alkylated product stream containing alkylbenzenes, unreacted benzene, $C_{10}$–$C_{15}$ paraffins, n-pentane, and possibly water flows through line 32 to benzene column 30. Benzene column 30 produces a bottom stream in line 34 which contains alkylbenzenes and paraffins and which is sent to conventional product recovery facilities (not shown).

Benzene column 30 also produces an overhead stream in line 36 that contains unreacted benzene, n-pentane, and possibly water. The overhead stream may also contain light naphthenes, such as cyclohexane. The overhead stream is partially condensed in condenser 38, and the condensed overhead stream flows through line 37 to combine with fresh makeup benzene which is charged through line 39. The combined stream flows through line 42 and enters overhead receiver 40. Overhead receiver 40 consists of a horizontally-oriented section 44 for separating the entering stream into a vapor and a liquid and a vertically-oriented water boot 50 for separating the liquid into a hydrocarbon phase and a water phase. The vapor phase, which typically contains light paraffins, and water vapor, is withdrawn from section 44 via line 46, and the water phase is withdrawn from boot 50 via line 48. The hydrocarbon phase, which contains benzene, n-pentane, and water flows through line 47 and divides into two portions. One portion is returned to benzene column 30 as reflux in line 52, and the other portion flows through line 49 to a drier 51, which contains a desiccant to remove water. After drying, this portion flows to dividing wall distillation column 60 via lines 53 and 83, for recovery of the n-pentane in the overhead stream of column 60.

Benzene column 30 also produces a benzene-containing sidedraw stream, which is withdrawn from column 30 via line 54. This sidedraw stream contains less water than the hydrocarbon phase flowing in line 47, since water tends to concentrate in the overhead stream flowing in line 36. Hence, this sidedraw stream is generally more desirable than the hydrocarbon phase for use elsewhere in the process. The sidedraw stream flowing in line 54 divides into four portions. One portion is recycled to the selective alkylation zone 28 via lines 56 and 58. A second portion flows to dividing wall distillation column 60 via lines 62, 82, and 83 to function as reflux in the feed-side portion of the middle zone of column 60. A third portion flows via line 62, line 64, valve 66, and line 68 to off-stream sorbent bed 70, where it acts as a desorbent to desorb aromatic byproducts from the sorbent in bed 70. Finally, the fourth portion flows to dividing wall distillation column 60 via line 55 to function as reflux below accumulator plate 98 in the sidedraw-side portion of the middle zone of column 60. Of course, any of the benzene-containing streams in FIG. 1, including the sidedraw stream in line 54, the four portions formed from the sidedraw stream, the vapor phase in line 46, the hydrocarbon phase in line 47, and the two portions of the hydrocarbon phase, may contain light hydrocarbons having boiling points that are close to that of benzene at the operating conditions of the benzene column 30. Such light hydrocarbons include light naphthenes, such as cyclohexane.

The two main feed streams to dividing wall distillation column 60 are the streams flowing through lines 136 and 78. The stream flowing in line 136 is in large part produced by purging off-stream sorbent bed 120. The effluent of off-stream sorbent bed 120, which contains n-pentane and $C_{10}$–$C_{15}$ paraffins, flows through line 126, valve 128, line 132, and enters mix drum 130. Fresh dry makeup n-pentane enters mix drum 130 via line 134. Since the flow rate and/or the composition of both the effluent in line 132 and the makeup stream in line 134 can change during a single purging step and/or from one purging step to the next, mix drum 130 provides a buffer or mixing volume to dampen the magnitude of these changes and help prevent upsets in the dividing wall distillation column 60. The flow rate of the effluent of mix drum 130 to column 60 is regulated by a flow controller (not shown) in line 136. The other main feed stream, the stream flowing in line 78, is produced by desorption of off-stream sorbent bed 70. The effluent of off-stream sorbent bed 70, which contains benzene, aromatic byproducts, n-pentane, and minor amounts of $C_{10}$–$C_{15}$ paraffins, flows through line 72, valve 74, line 76, and enters mix drum 80. Since the flow rate and/or the composition of the effluent in line 76 can change during a single desorption step and/or between desorption steps, mix drum 80 provides a buffer or mixing volume to dampen the magnitude of these changes and help prevent upsets in column 60. The flow rate of the effluent of mix drum 80 to column 60 is regulated by a flow controller (not shown) in line 78.

Dividing wall distillation column 60 contains a dividing wall 90 and plates, only some of which are designated in FIG. 1. Plates 84 and 86 are in the feed-side portion of the middle zone above and below, respectively, of the inlet of the drum effluent in line 78. Plate 102 is in the top zone above the inlet of the drum effluent in line 136 and plate 103 is in the top zone below that inlet. Plates 96 and 94 are in the sidedraw-side portion of the middle zone above and below, respectively of the sidedraw withdrawn in line 100. Plate 88 is in the bottom zone. Column 60 contains three accumulator plates, which are shown in FIG. 1. Accumulator plate 101 is at the top of dividing wall 90 and collects liquid flowing downward from the top zone and directs it to the sidedraw-side portion of the middle zone. Accumulator plate 98 and its associated downcomer 99 collect liquid flowing downward in the sidedraw-side portion of the middle zone and route it from the column 60 into line 100. Accumulator plate 92 is at the bottom of dividing wall 90 and collects liquid flowing downward from the middle zone and directs it into the bottom zone. Depending on the arrangement and configuration of plates in the middle and bottom zones, accumulator plate 92 may be omitted.

An overhead stream comprising n-pentane is recovered from the top of the dividing wall distillation column 60 and passes via line 104 to condenser 106. Using a suitable cooling medium, condenser 106 condenses a portion of the overhead steam and produces a two-phase condenser outlet stream comprising n-pentane-containing vapors and liquids. Condenser outlet stream in line 108 enters overhead receiver 110 where the phases separate into uncondensed vapors which leave receiver 110 via line 112 and liquid n-pentane which exits receiver 110 via line 114. A portion of the liquid n-pentane in line 114 refluxes to column 60 via line 116 with the remainder recycling to bed 120 via lines 118, valve 122, and line 124.

A bottom stream comprising aromatic byproducts is withdrawn from the bottom of dividing wall distillation column 60 via line 138. A portion of the stream in line 138 passes through line 144, is partially vaporized in reboiler 140 using any suitable heating medium, and returns to column 60 as a two-phase reboiler outlet stream via line 146. The remainder of the hydrocarbons in line 138 are rejected from the process via line 142. A sidedraw comprising benzene, $C_{10}$ to $C_{15}$ paraffins, and possibly a minor amount of n-pentane is withdrawn from column 60 through line 100, combines with recycle benzene in line 56, and passes to selective alkylation zone 28 via line 58. Any n-pentane that is carried with the sidedraw in line 100 into the selective alkylation zone 28 generally passes through the selective alkylation zone 28 without undergoing any significant reaction, is recovered in overhead receiver 40, and is recycled to dividing wall distillation column 60 via line 53. Similarly, any compounds that co-boil with benzene and which do not react to a significant extent in the selective alkylation zone 28, such as cyclohexane, pass through the selective alkylation zone 28, are recovered from column 30, and are recycled via sidedraw stream 54. Light byproducts that are formed by cracking side reactions in the selective alkylation zone 28 are removed from the process via lines 46 and 112.

FIG. 2 shows another embodiment of the subject invention wherein the purging and desorption effluents are separated in two thermally coupled distillation columns 210 and 220 rather than in a single dividing wall distillation column 60 as in FIG. 1. For the sake of brevity, items in FIG. 2 that correspond to items that have already been shown and described in FIG. 1 are not shown in or described for FIG. 2. Items in FIG. 2 that correspond to items in FIG. 1 have the same reference number, such as items numbers 55, 78, 83, 100, 112, 118, 136, and 142.

Referring now to FIG. 2, a stream produced in large part by desorbing the off-stream sorbent bed 70 flows via line 78 into preheat exchanger 212. In exchanger 212, the feedstock is heated by indirect heat exchange with a suitable heat exchange medium. The heated stream flows through line 214 and enters prefractionator 210. Prefractionator 210 contains plates, one of which is denoted as item 218. A prefractionator overhead stream is recovered from the top of prefractionator 210 via line 216 and passes to main column 220. A liquid stream flows from to the top of prefractionator 210 via line 83. A prefractionator bottom stream is recovered from the bottom of prefractionator 210 and flows through line 222 to main column 220.

Main column 220 contains plates, only some of which are designated in FIG. 2. Plate 256 is above the sidedraw 100, plate 250 is below the sidedraw and above the inlet of the prefractionator bottom stream, and plate 246 is below the inlet of the prefractionator bottom stream. Column 220 contains two accumulator plates, which are shown in FIG. 2. Accumulator plate 254 and its associated downcomer 252 collect liquid flowing downward in the main column 220 and route it from the column 220 into line 100. Accumulator plate 248 collects liquid flowing downward in the main column 220 and liquid from the prefractionator bottom stream and re-directs it to the lower plates, such as plate 246.

A main column vapor draw stream flows from main column 220 to the bottom of prefractionator 210 through line 224. A stream produced in large part by purging off-stream sorbent bed 120 flows via line 136 into the top zone of main column 220. A main column overhead stream comprising n-pentane is recovered from the top of main column 220 and passes via line 226 to condenser 228. Condenser 228 uses a suitable cooling medium and condenses a portion of the main column overhead steam and produces a two-phase condenser outlet stream comprising n-pentane vapors and liquids. The condenser outlet stream in line 232 enters overhead receiver 230 where the phases separate into uncondensed vapors which leave receiver 230 via line 112 and liquid n-pentane which exits receiver 230 via line 234. A portion of the n-pentane liquid in line 234 refluxes to main column 220 via line 236 with the remainder being recycled to bed 120 via lines 118, valve 122, and line 124.

A main column bottom stream comprising aromatic byproducts is withdrawn from the bottom of main column 220 via line 238. A portion of the aromatic byproducts in line 238 passes through line 242, is partially vaporized in reboiler 240 using any suitable heating medium, and returns to main column 220 as a two-phase reboiler outlet stream via line 244. The remainder of the aromatic byproducts in line 238 are rejected from the process via line 142. The sidedraw stream comprises benzene and $C_{10}$ to $C_{15}$ paraffins and passes to selective alkylation zone 28. A liquid stream comprising benzene is introduced to main column 220 via line 55 to function as reflux below accumulator plate 254.

EXAMPLE

The following example illustrates an embodiment of the invention for the separation of a desorption effluent containing benzene and aromatic byproducts, a purging effluent mainly containing n-pentane with some $C_{10}$–$C_{14}$ paraffin/olefins, and a drag stream mainly containing benzene. The separation recovers an overhead stream containing n-pentane and a sidedraw stream mainly containing benzene and the $C_{10}$–$C_{14}$ paraffin/olefins, and also produces a bottom stream mainly containing aromatic byproducts. The compositions of these six streams are shown in the Table. Two reflux streams are used in the separation, and their compositions are also shown in the Table. The concentration of n-pentane in the sidedraw stream is less than 0.1 mol-%, and the concentration of aromatic byproducts in the sidedraw stream is less than 0.1 mol-%. More than 99.9 mol-% of the benzene in the entering streams are recovered in the sidedraw stream. More than 99.9 mol-% of the n-pentane in the entering streams is recovered in the overhead stream. More than 99.9 mol-% of the entering aromatic byproducts is recovered in the bottom stream. Essentially all of the $C_{10}$–$C_{14}$ paraffin/olefin component(s) entering with the purging effluent stream is recovered in the sidedraw stream. This example is based on engineering calculations and scientific distillation predictions, and is not intended to limit the invention as set forth in the claims.

Figure 3:
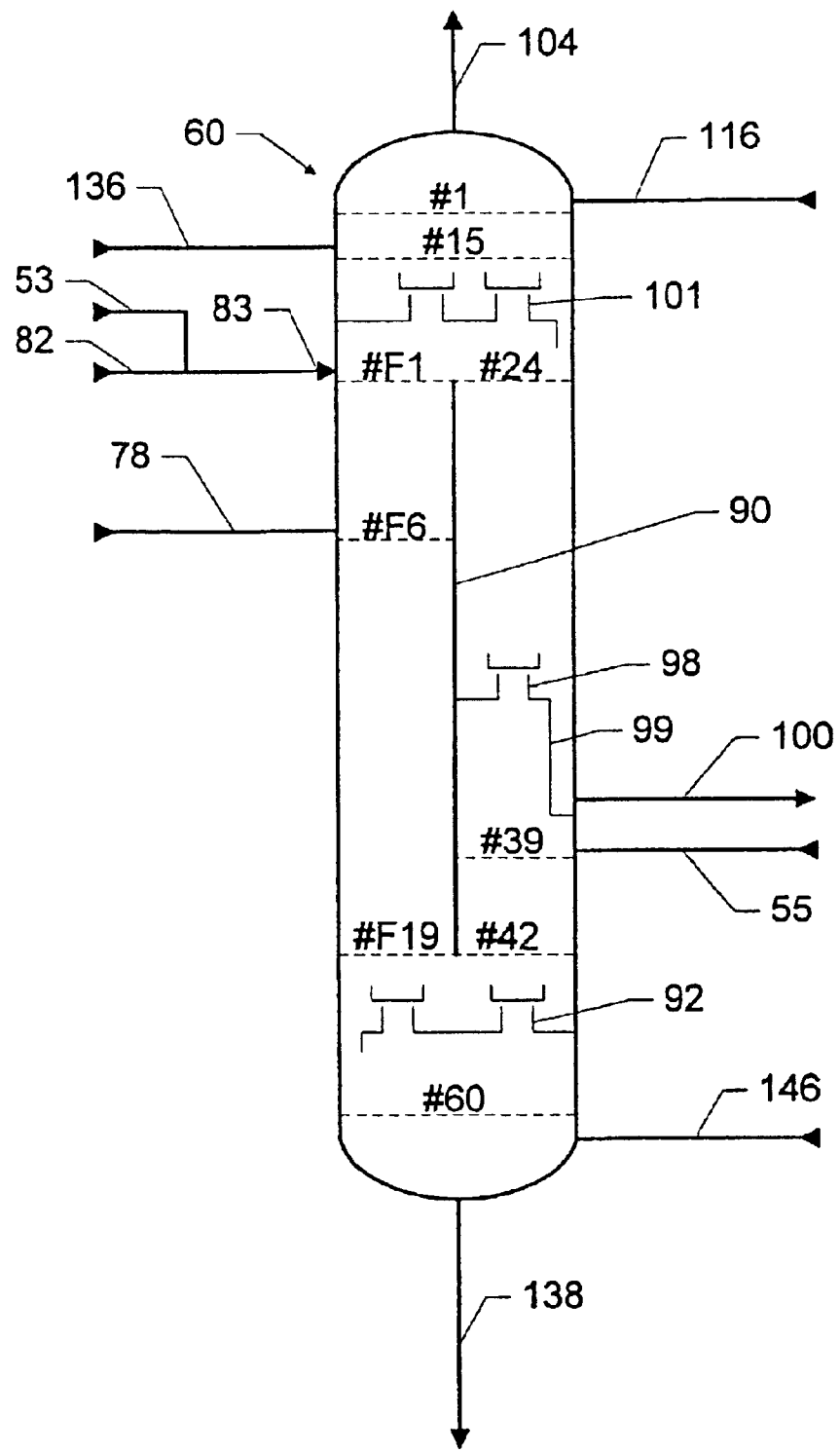

This example makes reference to FIG. 3, which shows a dividing wall distillation column 60 and which uses the same reference numbers as FIG. 1 to avoid unnecessary repetition. The trays in column 60 in this example have a plate efficiency of 80%. As used in this example, the term "tray" when used alone refers to a tray on which distillation occurs, while the term "accumulator tray" or "trap tray" refers to a tray which functions mainly to accumulate or trap liquid in a collection volume and which is not primarily used for distillation. Trays in FIG. 3 are denoted with numbers preceded by a "#" symbol to distinguish them from reference numbers. In contrast, accumulator trays or trap trays are denoted only with a reference number and not with a "#" symbol. Two tray numbering systems are used in FIG. 3. One system assigns numbers to trays in the feed-side portion of the middle zone in ascending order from the top to the bottom of the feed-side portion. In this numbering system, the tray at the top of dividing wall 90 is denoted tray #F1, which is also the tray at which reflux in line 83 enters distillation column 60. Four trays (not shown in FIG. 3) are between tray #F1 and the feed tray #F6 for the desorption effluent, and twelve trays (not shown) are between tray #F6 and tray #F19, which is in the feed-side portion of the middle zone at the bottom of dividing wall 90. The other numbering system numbers trays in the top zone, the sidedraw-side portion of the middle zone, and the bottom zone in ascending order from the top to the bottom of dividing wall distillation column 60. In this second system, the tray that is uppermost in dividing wall distillation column 60 and which is shown just below line 116 is denoted as tray #1, which is the tray at which reflux in line 116 enters distillation column 60. Thirteen trays (not shown) are between tray #1 and the feed tray #15 for the purging effluent, and eight trays (not shown) are between tray #15 and the accumulator tray 101, which is not deemed to be a fractionating tray and therefore is not numbered. Thus, tray #23 is the lowest tray in the top zone. Further down column 60 and on the sidedraw-side portion of the middle zone, the tray shown at the top of dividing wall 90 is tray #24. Tray #39, which is below accumulator tray 98, is the tray at which reflux in line 55 enters column 60, and tray #42 is the tray at the bottom of dividing wall 90 on the sidedraw-side portion of column 60. Below dividing wall 90 is accumulator tray 92, below which this second numbering system continues to tray #60, which is shown just above line 146 and is the lowermost tray in dividing wall distillation column 60. Thus, twenty-two trays (not shown) are in the top zone between tray #1 and tray #24. Fourteen trays (not shown) are between tray #24 and tray #39. Two trays (not shown) are in the sidedraw-side portion between tray #39 and tray #40. Finally, seventeen trays (not shown) are in the bottom zone between tray #42 and tray #60.

Referring now to FIG. 3, the desorption effluent and purging effluent are charged to dividing wall distillation column 60. The temperatures of the desorption effluent and the purging effluent are 266° F. (130° C.). In the feed-side portion of the middle zone, V/L is 9.7 between trays #F1 and #F6, V/L is 0.4 between trays #F6 and #F19, the temperature at tray #F1 is 228° F. (109° C.), and the temperature at tray #F26 is 252° F. (122° C.). In the top zone, V/L is 1.8 between uppermost tray #1 and tray #15, V/L is 1.1 between tray #15 and accumulator tray 101. In the sidedraw-side portion of the middle zone, V/L is 0.7 between tray #24 and accumulator tray 98, V/L is 3.9 between trays #39 and #42, the temperature at tray #24 is 216° F. (102° C.), and the temperature at tray #42 is 252° F. (122° C.). In the bottom zone, V/L is 1.0 between accumulator tray 92 and tray #60.

Compared to using the previously-described two column prior art process to separate the same three streams—desorption effluent, purging effluent, and drag stream—to produce three streams having the same compositions as the overhead stream, the sidedraw stream, and the bottom stream as in this example, this invention needs only one reboiler with a duty of 9.3 MMBTU/hr (2.7 MW), whereas the prior art process needs two reboilers having a combined duty of 18.1 MMBTU/hr (5.3 MW), despite the fact that the streams in lines 60 and 82 circulate about 24% more benzene through column 60 than is circulated through the two columns of the prior art process. Thus, this invention not only eliminates a column including its reboiler but also decreases the reboiler energy requirements by 49%.

TABLE

| Stream Name | Desorption effluent | Purging effluent | Drag stream | Reflux stream | Reflux stream | Overhead stream | Sidedraw stream | Bottom stream |
| --- | --- | --- | --- | --- | --- | --- | --- | --- |
| Line No. in FIG. 1 | 78 | 136 | 53 | 60 | 82 | 118 | 100 | 142 |
| Component concentration, mol-%: | | | | | | | | |
| n-Pentane | 12.7 | 92.1 | 3.6 | 0.0 | 0.0 | 100.0 | 0.0 | 0.0 |
| Benzene | 82.3 | 0.0 | 88.8 | 92.1 | 92.1 | 0.0 | 89.8 | 2.0 |
| Cyclohexane | 3.8 | 0.0 | 7.6 | 7.9 | 7.9 | 0.0 | 4.9 | 0.0 |
| $C_{10}$–$C_{14}$ Paraffins and Olefins | 0.3 | 7.9 | 0.0 | 0.0 | 0.0 | 0.0 | 5.3 | 27.9 |
| Aromatic byproducts | 0.9 | 0.0 | 0.0 | 0.0 | 0.0 | 0.0 | 0.0 | 70.1 |
| TOTAL | 100.0 | 100.0 | 100.0 | 100.0 | 100.0 | 100.0 | 100.0 | 100.0 |

What is claimed is:

1. A process for producing a product aromatic compound, the process comprising:

a) dehydrogenating a feed stream comprising a $C_6$–$C_{22}$ paraffin in a dehydrogenation zone and recovering therefrom a dehydrogenated product stream comprising a monoolefin and aromatic byproducts;

b) selectively removing at least a portion of the aromatics byproducts from the dehydrogenated product stream by at least intermittently passing at least a portion of the dehydrogenated product stream to an on-stream aromatic byproducts removal zone containing sorbent at conditions effective to selectively sorb the aromatic byproducts on the sorbent and to produce a sorption effluent stream comprising the monoolefin;

c) passing at least a portion of the sorption effluent stream to a selective alkylation zone and selectively alkylating a feed aromatic compound by reacting the feed aromatic compound and the monoolefin in the selective alkylation zone to form a product aromatic compound;

d) recovering from the selective alkylation zone an alkylated product stream comprising the product aromatic compound;

e) at least intermittently passing a purge stream comprising a purge component to an off-stream purge aromatic byproducts removal zone containing sorbent, wherein the sorbent in the off-stream purge aromatic byproducts removal zone is contained in a sorbent bed having a void volume and wherein the void volume contains the $C_6$–$C_{22}$ paraffin or the monoolefin, to displace the $C_6$–$C_{22}$ paraffin or the monoolefin from the void volume of the sorbent bed in the off-stream purge aromatic byproducts removal zone, and producing a purging effluent stream comprising the purge component and at least one of the $C_6$–$C_{22}$ paraffin and the monoolefin;

f) at least intermittently passing a desorbent stream comprising a desorption component to an off-stream desorption aromatic byproducts removal zone containing sorbent, wherein the sorbent in the off-stream desorption aromatic byproducts removal zone contains sorbed aromatic byproducts, to desorb aromatic byproducts from the sorbent in the off-stream desorption aromatic byproducts removal zone, and producing a desorption effluent stream comprising the desorption component and the aromatic byproducts;

g) at least intermittently passing at least a portion of the desorption effluent stream to a prefractionator distillation column;

h) separating the compounds entering the prefractionator distillation column at distillation conditions to provide a prefractionator overhead stream comprising the desorption component and a prefractionator bottom stream comprising the aromatic byproducts;

i) at least intermittently passing at least a portion of the prefractionator overhead stream to a main distillation column, and at least intermittently passing at least a portion of the prefractionator bottom stream to the main distillation column, wherein the prefractionator distillation column and the main distillation column are at least partially thermally coupled;

j) at least intermittently passing at least a portion of the purging effluent stream to the main distillation column;

k) separating the compounds entering the main distillation column to provide a main overhead stream comprising the purge component, a first main sidedraw stream comprising the desorption component, a second main sidedraw stream comprising the desorption component, and a main bottom stream comprising the aromatic byproducts;

l) at least intermittently passing at least a portion of the second main sidedraw stream to the prefractionator distillation column; and m) periodically shifting the functions of the on-stream aromatic by-products removal zone, the off-stream purge aromatic byproducts removal zone, and the off-stream desorption aromatic byproducts removal zone by operating the on-stream aromatic byproducts removal zone to function as the off-stream purge aromatic byproducts removal zone, operating the off-stream purge aromatic byproducts removal zone to function as the off-stream desorption aromatic byproducts removal zone, and operating the off-stream desorption aromatic byproducts removal zone to function as the on-stream aromatic byproducts removal zone.

2. The process of claim 1 further comprising:

n) withdrawing the first main sidedraw stream comprising the desorption component from an intermediate portion of the main distillation column, wherein the intermediate portion extends from a lower portion of the main distillation column to an upper portion of the main distillation column;

o) withdrawing the main overhead stream from the upper portion of the main distillation column, at least partially condensing the main overhead stream to form a main condensed stream comprising the purge component, refluxing a portion of the main condensed stream to the distillation column, and recovering the purge component from at least one of the main overhead stream and the main condensed stream; and p) introducing heat to the lower portion of the main distillation column, and withdrawing the second main sidedraw stream comprising the desorbent compound and the main bottom stream comprising the aromatic byproducts from the lower portion of the main distillation column.

3. The process of claim 1 wherein the first main sidedraw stream comprises at least one of the $C_6$–$C_{22}$ paraffin and the monoolefin.

4. The process of claim 1 further characterized in that at least a portion of the purge stream is provided from at least a portion of the overhead stream.

5. The process of claim 1 wherein the purge component comprises a $C_4$–$C_6$ paraffin.

6. The process of claim 1 wherein the desorption component comprises benzene.

7. The process of claim 1 further characterized in that the desorption component and the feed aromatic compound are the same compound.

8. The process of claim 7 further characterized in that at least a portion of the feed aromatic compound selectively alkylated in the alkylation zone is provided from at least a portion of the first main sidedraw stream.

9. The process of claim 7 further characterized in that a recycle stream comprising the feed aromatic compound is recovered from the selective alkylation zone and at least a portion of the desorbent stream is provided from at least a portion of recycle stream.

10. The process of claim 1 further characterized in that the at least a portion of the purging effluent stream passes to an upper portion of the main distillation column, the upper portion of the main distillation column is above an intermediate portion of the main distillation column, the $C_6$–$C_{22}$ paraffin or the monoolefin in the upper portion of the distillation column passes in the liquid phase from the upper portion of the main distillation column to the intermediate portion of the main distillation column, and the desorption compound in the intermediate portion of the main distillation column passes in the vapor phase from the intermediate portion of the main distillation column to the upper portion of the main distillation column.

11. The process of claim 10 further characterized in that essentially none of the $C_6$–$C_{22}$ paraffin or the monoolefin in the upper portion of the main distillation column passes from the upper portion to the prefractionator distillation column.

12. The process of claim 1 further characterized in that the at least a portion of the desorption effluent is introduced to the prefractionator distillation column at a first elevation, and a liquid-phase stream comprising the desorption component is introduced to the prefractionator distillation column at a second elevation that is above the first elevation.

13. The process of claim 12 further characterized in that a recycle stream comprising the feed aromatic compound is recovered from the selective alkylation zone, the desorption component and the feed aromatic compound are the same compound, and at least a portion of the liquid-phase stream is provided from at least a portion of recycle stream.

14. The process of claim 1 further characterized in that the main distillation column has an vertically-oriented intermediate portion, the intermediate portion is divided into an upper zone and a lower zone by a horizontally extended partition, the first main sidedraw stream is withdrawn from the upper zone, the $C_6$–$C_{22}$ paraffin or the monoolefin in the upper zone is withdrawn from the upper zone in the first main sidedraw stream in the liquid phase, and the desorption component in the lower zone passes in the vapor phase from the lower zone to the upper zone.

15. The process of claim 14 further characterized in that essentially none of the $C_6$–$C_{22}$ paraffin or the monoolefin in the upper zone passes from the upper zone to the lower zone.

16. The process of claim 14 further characterized in that a liquid-phase stream comprising the desorption component is introduced to the lower zone.

17. The process of claim 16 further characterized in that a recycle stream comprising the feed aromatic compound is recovered from the selective alkylation zone, the desorption component and the feed aromatic compound are the same compound, and at least a portion of the liquid-phase stream is provided from at least a portion of the recycle stream.

18. The process of claim 1 further characterized in a drag stream comprising the feed aromatic compound and the purge component is recovered from the selective alkylation zone, the desorption component and the feed aromatic compound are the same compound, and the drag stream is introduced to the prefractionator distillation column.

19. The process of claim 1 further characterized in that more than 99% of the aromatic byproducts in the dehydrogenated product stream are recovered in the main bottom stream.

20. The process of claim 1 further characterized in that the prefractionator distillation column and the main distillation column are thermally coupled.

21. The process of claim 20 wherein the prefractionator distillation column and the main distillation column are fully thermally coupled.

22. A process for producing a product aromatic compound, the process comprising:
a) dehydrogenating a feed stream comprising a $C_6$–$C_{22}$ paraffin in a dehydrogenation zone and recovering therefrom a dehydrogenated product stream comprising a monoolefin and aromatic byproducts;
b) selectively removing at least a portion of the aromatics byproducts from the dehydrogenated product stream by at least intermittently passing at least a portion of the dehydrogenated product stream to an on-stream aromatic byproducts removal zone containing sorbent at conditions effective to selectively sorb the aromatic byproducts on the sorbent and to produce a sorption effluent stream comprising the monoolefin;
c) passing at least a portion of the sorption effluent stream to a selective alkylation zone and selectively alkylating a feed aromatic compound by reacting the feed aromatic compound and the monoolefin in the selective alkylation zone to form a product aromatic compound;
d) recovering from the selective alkylation zone an alkylated product stream comprising the product aromatic compound;
e) at least intermittently passing a purge stream comprising a purge component to an off-stream purge aromatic byproducts removal zone containing sorbent, wherein the sorbent in the off-stream purge aromatic byproducts removal zone is contained in a sorbent bed having a void volume and wherein the void volume contains the $C_6$–$C_{22}$ paraffin or the monoolefin, to displace the $C_6$–$C_{22}$ paraffin or the monoolefin from the void volume of the sorbent bed in the off-stream purge aromatic byproducts removal zone, and producing a purging effluent stream comprising the purge component and at least one of the $C_6$–$C_{22}$ paraffin and the monoolefin;
f) at least intermittently passing a desorbent stream comprising a desorption component to an off-stream desorption aromatic byproducts removal zone containing sorbent, wherein the sorbent in the off-stream desorption aromatic byproducts removal zone contains sorbed aromatic byproducts, to desorb aromatic byproducts from the sorbent in the off-stream desorption aromatic byproducts removal zone, and producing a desorption effluent stream comprising the desorption component and the aromatic byproducts;
g) at least intermittently passing at least a portion of the desorption effluent stream to a first lateral section of an intermediate portion of a distillation column at distillation conditions, wherein the first lateral section is separated from a second lateral section of the intermediate portion of the distillation column by a vertically oriented baffle extending upward from a lower portion of the distillation column to an upper portion of the distillation column;
h) at least intermittently passing at least a portion of the purging effluent stream to the upper portion of the distillation column;
i) separating the compounds entering the distillation column to provide an overhead stream comprising the purge component, a sidedraw stream comprising the desorption component, and a bottom stream comprising the aromatic byproducts; and
j) periodically shifting the functions of the on-stream aromatic by-products removal zone, the off-stream purge aromatic byproducts removal zone, and the off-stream desorption aromatic byproducts removal zone by operating the on-stream aromatic byproducts removal zone to function as the off-stream purge aromatic byproducts removal zone, operating the off-stream purge aromatic byproducts removal zone to function as the off-stream desorption aromatic byproducts removal zone, and operating the off-stream desorption aromatic byproducts removal zone to function as the on-stream aromatic byproducts removal zone.

23. The process of claim 22 further comprising:
k) at least partially condensing the overhead stream to form a condensed stream comprising the purge component, refluxing a portion of the condensed stream to the distillation column, and recovering the purge component from the overhead stream;
l) introducing heat to the lower portion of the distillation column, and withdrawing the bottom stream comprising the aromatic byproducts from the lower portion of the distillation column; and m) withdrawing the sidedraw stream comprising the desorption component from the second lateral section of the distillation column.

24. The process of claim 22 wherein the sidedraw stream comprises at least one of the $C_6$–$C_{22}$ paraffin and the monoolefin.

25. The process of claim 22 further characterized in that at least a portion of the purge stream is provided from at least a portion of the overhead stream.

26. The process of claim 22 wherein the purge component comprises a $C_4$–$C_6$ paraffin.

27. The process of claim 22 wherein the desorption component comprises benzene.

28. The process of claim 22 further characterized in that the desorption component and the feed aromatic compound are the same compound.

29. The process of claim 28 further characterized in that at least a portion of the feed aromatic compound selectively alkylated in the alkylation zone is provided from at least a portion of the sidedraw stream.

30. The process of claim 28 further characterized in that a recycle stream comprising the feed aromatic compound is recovered from the selective alkylation zone and at least a portion of the desorbent stream is provided from at least a portion of recycle stream.

31. The process of claim 22 further characterized in that the upper portion of the distillation column is separated from the first lateral section of the intermediate portion of the distillation column by a horizontally extended partition, the $C_6$–$C_{22}$ paraffin or the monoolefin in the upper portion of the distillation column passes in the liquid phase from the upper portion to the second lateral section, and the desorption compound in the first lateral section of the intermediate portion of the distillation column passes in the vapor phase from the first lateral section to the upper portion of the distillation column.

32. The process of claim 31 further characterized in that essentially none of the $C_6$–$C_{22}$ paraffin or the monoolefin in the upper portion of the distillation column passes from the upper portion to the first lateral section.

33. The process of claim 31 further characterized in that the first lateral section is vertically oriented, the at least a portion of the desorption effluent is introduced to the first lateral section at a first elevation, and a liquid-phase stream comprising the desorption component is introduced to the first lateral section at a second elevation that is above the first elevation.

34. The process of claim 33 further characterized in that a recycle stream comprising the feed aromatic compound is recovered from the selective alkylation zone, the desorption component and the feed aromatic compound are the same compound, and at least a portion of the liquid-phase stream is provided from at least a portion of recycle stream.

35. The process of claim 22 further characterized in that the second lateral section of the intermediate portion of the distillation column is vertically oriented, the second lateral section is divided into an upper zone and a lower zone by a horizontally extended partition, the sidedraw stream is withdrawn from the upper zone, the $C_6$–$C_{22}$ paraffin or the monoolefin in the upper zone is withdrawn from the upper zone in the sidedraw stream in the liquid phase, and the desorption component in the lower zone passes in the vapor phase from the lower zone to the upper zone.

36. The process of claim 35 further characterized in that essentially none of the $C_6$–$C_{22}$ paraffin or the monoolefin in the upper zone passes from the upper zone to the lower zone.

37. The process of claim 35 further characterized in that a liquid-phase stream comprising the desorption component is introduced to the lower zone.

38. The process of claim 37 further characterized in that a recycle stream comprising the feed aromatic compound is recovered from the selective alkylation zone, the desorption component and the feed aromatic compound are the same compound, and at least a portion of the liquid-phase stream is provided from at least a portion of the recycle stream.

39. The process of claim 22 further characterized in that a drag stream comprising the feed aromatic compound and the purge component is recovered from the selective alkylation zone, the desorption component and the feed aromatic compound are the same compound, and the drag stream is introduced to the distillation column.

40. The process of claim 39 further characterized in that the drag stream is introduced to the first lateral section of the distillation column.

41. The process of claim 22 further characterized in that more than 99% of the aromatic byproducts in the dehydrogenated product stream are recovered in the bottom stream.

* * * * *